United States Patent [19]

Jeppsson et al.

[11] Patent Number: 5,722,947
[45] Date of Patent: Mar. 3, 1998

[54] APPARATUS FOR CARRYING OUT PERITONEAL DIALYSES

[75] Inventors: Jan-Bertil Jeppsson, Lomma; Tor Nordlie, Eslov, both of Sweden

[73] Assignee: Gambro AB, Sweden

[21] Appl. No.: 687,596

[22] PCT Filed: Jan. 30, 1995

[86] PCT No.: PCT/SE95/00086

§ 371 Date: Sep. 17, 1996

§ 102(e) Date: Sep. 17, 1996

[87] PCT Pub. No.: WO95/20985

PCT Pub. Date: Aug. 10, 1995

[30] Foreign Application Priority Data

Feb. 3, 1994 [SE] Sweden .............................. 9400347

[51] Int. Cl.$^6$ .................................................. A61M 1/00
[52] U.S. Cl. .................. 604/29; 128/DIG. 12; 128/DIG. 13; 604/67
[58] Field of Search .................. 664/29, 65–67, 664/30–34, 49–53

[56] References Cited

U.S. PATENT DOCUMENTS 4,412,917  11/1983  Ahjopalo .
4,413,988  11/1983  Handt et al. .

Primary Examiner—Michael Buiz
Assistant Examiner—Manuel Mendez
Attorney, Agent, or Firm—Lerner, David, Littenberg, Krumholz & Mentlik

[57] ABSTRACT

Apparatus for carrying out peritoneal dialysis. The apparatus comprises a weighing device (37) provided with a case (50) for forming an airtight space. A heat bag (38) and, optionally, a discharge bag (42) are positioned in the space, said bags being connected with a catheter for the patient, who is to perform peritoneal dialysis. The apparatus comprises a pump arrangement (57) connected with the case (50) for producing overpressure and underpressure, respectively, in the space inside the case. Valve arrangements (39, 44) are adapted to connect either the discharge bag (42) or the heat bag (38) with the patient's catheter. By providing an underpressure in the case (50), fresh dialysis solution is provided to the heat bag (38) from supply bags, whereupon used dialysis fluid is extracted from a patient to the discharge bag (42). By causing an overpressure in the case (50), a fresh and heated dialysis solution is supplied from the heat bag (38) to the patient, whereupon the discharge bag (42) is drained to a waste or to collection bags. The flow of dialysis solution is monitored by the apparatus by means of weighing the case (50) and its contents. Suitable data for the treatment is stored in a memory unit of the apparatus.

25 Claims, 9 Drawing Sheets

APPARATUS FOR CARRYING OUT PERITONEAL DIALYSES

FIELD OF THE INVENTION

The present invention relates to an apparatus for administering peritoneal dialysis solution to a patient, such apparatus being known as a PD-cycler.

STATE OF THE ART

The invention starts out from the technology which is used by the applicant in the GAMBRO PD 100 system. This system comprises of a stand which is about 2 meters high. At a first upper level, at the upper end of the stand, there are hooks for hanging bags containing ready-mixed supply solution for peritoneal dialysis. The supply bags are connected via tubes to a heat bag positioned just below the supply bags at a second intermediate level. The heat bag is positioned on a heating surface of a weighing device.

The heat bag is filled, under control of valves, from the supply bags and may have a volume of about 2 liters or slightly more. When the contents in the heat bag has obtained the correct temperature, this is fed by gravity to a catheter terminating in the abdominal cavity of the patient. The catheter and the abdominal cavity are at a third level which is below the second level.

When the dialysis solution has fulfilled its task it is drained to a discharge bag positioned on a fourth level. The discharge bag is attached to a hook arrangement which hangs on the weighing device for the heat bag. In this way the same weight measuring element or load cell is used for weighing the heat bag as well as the discharge bag. The contents of the discharge bag is finally drained either directly to a drain or to collection bags which are situated on a fifth and lowest level. All transport of solution occurs by means of gravity between the five different levels. It is obviously important that the patient is situated at a particular level below the heat bag and above the discharge bag.

A tube-set intended for use in the GAMBRO PD 100 system is shown in EP-A1-499 718.

A similar cycler system is described in U.S. Pat. No. 5,141,492 in which only three levels are used. In this case the input amount is not weighed but only determined by the size of the supply bags. The supply bags are heated directly to the appropriate temperature. The discharge bag is also used for collection and is dimensioned to be sufficiently large. Only the collection bag is weighed.

In order to avoid dependence on gravity for feeding the dialysis solution it has been suggested that pump arrangements be used for this purpose. Such a pump arrangement is disclosed in U.S. Pat. No. 4,412,917 in the form of a peristaltic pump for feeding dialysis solution to a patient from a supply container positioned at floor level. A pressure monitoring arrangement insures that the pressure to the catheter does not exceed a predetermined value. The supply container as well as the collection container are positioned on a weighing device for monitoring the inlet and outlet of dialysis solution to and from the patient.

U.S. Pat. No. 4,560,472 discloses a pump arrangement for pumping supply solution from a first level to a heat bag positioned at a higher level. The continued transport of the dialysis solution occurs thereafter by means of gravity. In this way the need to lift the heavy supply bags up to a high level is avoided.

U.S. Pat. No. 5,004,459 discloses an even more automated system for administering PD-solution. The apparatus comprises i.a. a separate filling pump for filling the abdominal cavity and a separate outlet pump for extraction from the abdominal cavity. Two pressure and/or flow sensors detect and limit the pressure and/or flow for the supply and extraction. The apparatus further comprises mixing of dialysis concentrates with pure water, possibly with the addition of glucose.

U.S. Pat. No. 4,311,587 discloses a supply arrangement for dialysis solution through a sterile filter. The object is to avoid peritonitis by filtering the incoming solution. Since the sterile filter implies a large flow resistance, a higher pressure is required than that which can practically be achieved by means of gravity. Thus a bag containing dialysis solution is placed in a belt under the arm and manual pressure is applied with the armor elbow to the bag in order to press the dialysis solution through the sterile filter and through the catheter into the abdominal cavity. Extraction occurs with the help of gravity. One-way valves are used in this construction.

U.S. Pat. No. 5,141,493 discloses a system where a pump and a pressure sensor are used for supplying and extracting a dialysis solution to and from a patient. The dialysis solution is then circulated in a primary circuit through a dialyser which in turn is connected with a secondary circuit, whereby the dialysis solution in the first circuit is cleaned with the help of said dialyser.

WO 90/13795 discloses a pump arrangement intended i.a. for use in connection with peritoneal dialysis. The pump arrangement consists of a chamber divided by an elastic membrane. On one side of the membrane is the solution which is to be pumped and on the other side of the membrane there is gas. Positive and negative pressure is supplied to the chamber with gas. The pumped volume is monitored and measured by measuring the gas volume in the chamber for gas.

EP-A1-94 682 discloses a device for reinfusion of blood, comprising a vessel having rigid walls enclosing a flexible container. Blood is fed into the flexible container by exerting a subpressure in the space between the container and the vessel. Then, the blood is reinfused by exerting an overpressure in the space between the container and the vessel.

SUMMARY OF THE INVENTION

A first object of the present invention is to provide an apparatus for peritoneal dialysis where the supply and/or extraction of the dialysis solution to and/or from the patient occurs entirely or partly without the help of gravity, i.e. with the help of pump arrangements. In this way it is possible for the patient to adopt different positions with respect to the apparatus without affecting the function of the apparatus. Additionally, higher pressure can be used than that which is practically possible with supply by means of gravity, which reduces the supply and extraction times. At the same time, the flow rates can be adapted to the demands of a specific patient.

A second object is to provide such a pump arrangement which is safe and convenient to use and which is sufficent silent for night operation.

A further object of the invention is to simplify the tube-set which is required for operating the apparatus for peritoneal dialysis.

It is desirable to obtain a pump function without the use of a pump which will be contaminated by dialysis solution. The obvious choice is for example a peristaltic pump (as shown in U.S. Pat. No. 4,412,917), which influences upon the tubes in the system without itself becoming contaminated.

In this regard it is noted that the dialysis solution passes through and is heated by the heat bag in the earlier known PD 100 system. According to the present invention such heat bag is used as a part of a pump arrangement by subjecting the heat bag to overpressure and/or underpressure. The flow to and from the heat bag is monitored continually by means of the weighing device.

The invention thus relates to an apparatus for carrying out peritoneal dialysis comprising a weighing device adapted for weighing the contents in a first flexible container, such as the heat bag, which is connected to at least one conduit as an outlet and possibly even as an inlet for a solution from the container. According to the invention the apparatus comprises a case which is arranged to surround the container so that a space is formed between the case and the container, whereby the container includes an introduction device for introducing the conduit through the casing. The apparatus further comprises a pressure device arranged to exert a pressure on the container for emptying thereof.

The apparatus suitably comprises an arrangement for supplying a pressure medium under overpressure and/or underpressure to the space between the case and the container, said space being closed. The case is preferably rigid.

The pressure medium is suitably a gas such as air, but can also be a fluid such as water. The case can consist of a lower part and an upper part. The lower part forms a weighing scale and is connected to the weighing device. The upper part can be folded away or removed from the lower part, the parts normally being sealed relative to one another. The case is connected to a pump arrangement in order to pump pressure medium in and/or out of the space between the case and the container.

The case can also comprise a second flexible container provided with a conduit for the inlet and/or outlet of a used or spent solution, whereby the first container is intended for fresh solution. Additionally there are valve arrangements for controlling the flow of solution to and from the containers which are suitably plastic bags.

The pump arrangement can be of the centrifugal pump type which achieves a predetermined pressure at its outlet and is reversed in order to achieve said underpressure. Alternatively, the pump can be a membrane pump controlled by a pressure sensor. Still alternatively, two pressure chambers can be used for underpressure and overpressure, whereby the volume of the case is successively connected with respective pressure chambers. A pump can work more or less continually and build up the pressure in the pressure chambers. A pressure monitoring device is used to monitor and regulate the pressure.

The advantages of the present invention with respect to the prior art are many.

1. Heavy lifting of the supply solution to a high level is no longer required.
2. The heat bag can be filled more quickly since the pressure during this process can be higher.
3. The discharge bag can be emptied into a waste located at a higher position.
4. The discharge bag comprises slag products which make the fluid more viscous, such as fibrin precipitates etc., but by using a higher pump pressure the extraction can occur more quickly.
5. Both the supply and extraction pressure to the patient can be adjusted according to that which the patient feels is comfortable.
6. The dialysis solution is always located inside bags and tubes which can be manufactured of cheap plastic material according to known techniques. The pump arrangement according to the invention only acts upon the outside of these bags. The PD-solution is located in a closed system for the whole time.
7. The apparatus according to the invention is simple and can be manufactured compactly and lightly, which means that it can easily be transported.
8. The apparatus is very flexible and can use combinations of forced supply and supply by means of gravity.
9. The apparatus according to the invention can work without appreciable energy consumption. The energy consumption can additionally be reduced so that the apparatus, for instance during a power cut, can operate for a longer time using reserve power such as batteries.
10. Additional energy saving can be made via heat exchanging of the warm dialysis solution in the discharge bag with colder fresh PD-solution in the heat bag.

DESCRIPTION OF THE DRAWINGS

Further objects, advantages and features will appear from the following detailed description of the invention with reference to certain preferred embodiments of the invention shown in the accompanying drawings.

DESCRIPTION OF PREFERRED EMBODIMENTS

Figure 1:
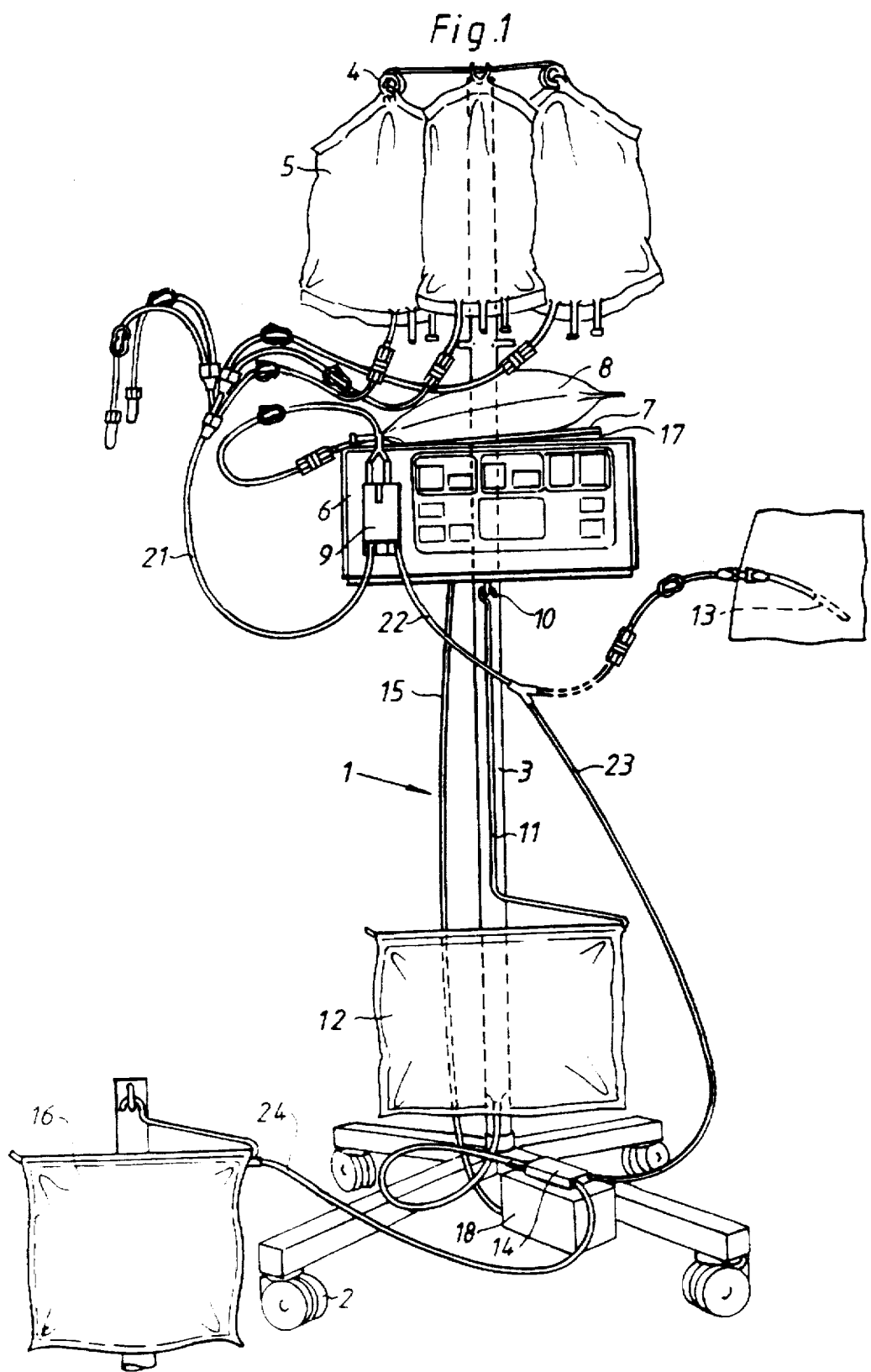
FIG. 1 is a perspective view of a PD-cycler according to the applicant's earlier known GAMBRO PD 100 system.

FIG. 1 shows an apparatus according to GAMBRO PD 100 system. The apparatus comprises a stand 1 supported at the base by five wheel arrangements 2. The stand comprises a vertical column 3 which is about 2 meters high. At the upper end of this there are several hook arrangements 4 for hanging up supply bags 5 containing dialysis solution. On an intermediate level of the stand there is a holder (not shown) for a regulating unit 6. At the bottom of the stand there is an additional holder 18 for a valve device 14.

The regulating unit 6 comprises scales 7, on which a heat bag 8 is positioned. The scales 7 are coupled to a load cell which measures the weight of the contents in the heat bag 8. On the regulating unit's 6 front side there are push buttons and displays which are used in order to control and reset the operating condition of the apparatus. The regulating unit 6 further comprises a valve arrangement 9 intended to operate on the tubes which connect the supply bags 5 with the heat bag 8.

The regulating unit 6 is further provided with a hook device 10 which is connected with the aforementioned load cell. A carrier device 11 is hung on the hook arrangement 10, said carrier arrangement supporting a discharge bag 12 at its lower end.

The supply bags 5, the heat bag 8, a catheter 13 entered into the abdominal cavity of the patient, the discharge bag 12 and a collection bag 16 are connected by means of a tube-set 20 which is shown in more detail in FIG. 2, and described below.

The holder 18 at the bottom end of the stand further comprises a valve arrangement 14 which is controlled by the regulating unit via a cable 15.

The valve arrangements 9 and 14 are double valve devices which clamp around the tubes which pass through the valve arrangements and thereby perform valve functions. The function of the valve arrangements 9 and 14 is such that when the one valve of each valve arrangement 9, 14 is opened, the corresponding other valve is closed.

As is clear from FIG. 1 the supply bags 5 are connected to heat bag 8 by a first tube 21 which passes through the valve arrangement 9. The heat bag 8 is connected with the patient's catheter 13 via a second tube 22 which also passes through the valve arrangement 9. The patient's catheter 13 is connected with the discharge bag 12 via a third tube 23 and the discharge bag 12 is connected with the collection bag 16 via a fourth tube 24, whereby the third and the fourth tube pass through the second valve arrangement 14.

Figure 2:
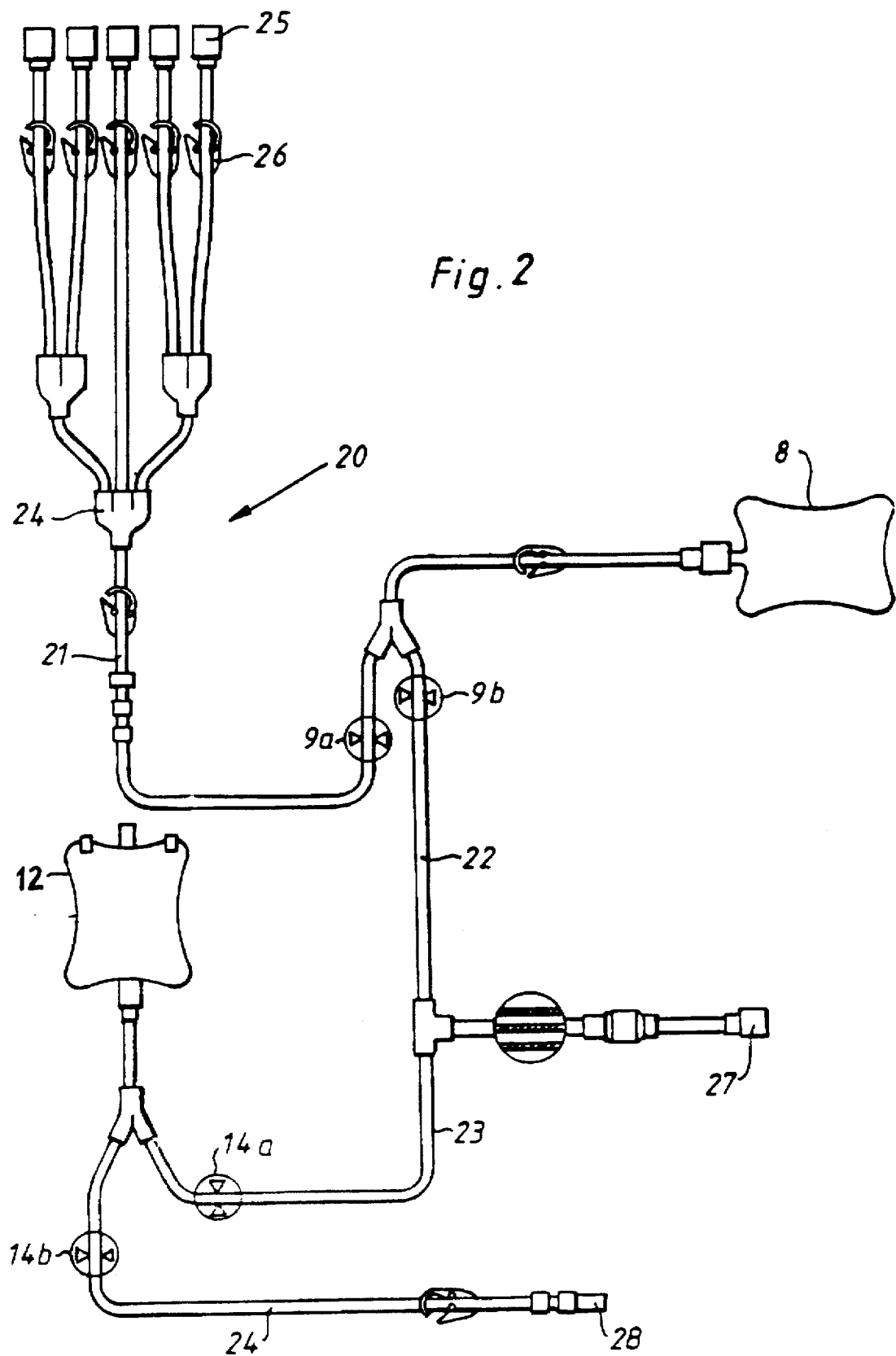
FIG. 2 is a side view of a tube-set for use in the GAMBRO PD 100 system.

The tube-set 20 is shown in more detail in FIG. 2. In this figure five connectors 25 are shown for five supply bags. The connectors 25 are connected with the first tube 21 via several tubes and a branch or manifold coupling 29. The outlet from each supply bag is regulated by each a tube clamp 26. The first tube 21 and the second tube 22 are connected with each other by a Y-coupling which then leads further to the heat bag 8. The first tube 21 has a clamp arrangement 9a and the second tube 22 has a clamp arrangement 9b, which are included in the first valve arrangement 9. The second tube 22 and the third tube 23 are connected to each other with a T-coupling which leads to a connector 27 to the patient's catheter. The tube between the connector 27 and the T-coupling can be of the double-type with separate inlet and outlet, so-called double-lumen tube. The third tube 23 and the fourth tube 24 are connected with each other by a Y-coupling which is further connected with the discharge bag 16. The third tube 23 has a clamp arrangement 14a and the fourth tube 24 has a clamp arrangement 14b which constitutes the second valve arrangement 14.

The fourth tube 24 ends with a connector 28 to a collection bag. A plurality of clamp arrangements similar to the clamp 26 are found at different locations on the tubes in order to allow manual manoeuvring and throttling of corresponding tubes.

The function of the PD 100 system as described above is as follows.

Filling of the heat bag (HF, Heater Fill)

When the valve arrangement 9 is in its first open position, the tube 21 is open. The dialysis solution is thereby fed from the supply bags 5 to the heat bag 8 by means of gravity. When the heat bag 8 is filled by the required amount, the valve arrangement 9 is closed and a measured amount of dialysis solution is stored in a memory of the regulating unit 6. The heat bag 8 is continually heated by a heat element 17 positioned in the scales 7 until the desired temperature has been reached.

Extraction of dialysis solution (PD, Patient Drain)

When the second valve arrangement 14 is in its first open position, the tube 23 is opened and connects the catheter 13 with the discharge bag 12. In this way, used dialysis solution is drained by means of gravity from the catheter 13 to the discharge bag 12. After a predetermined time the valve arrangement 14 is closed and collected dialysis solution in the discharge bag 12 is weighed with the help of the load cell in the regulating unit 6 and is stored in the regulating unit's memory.

Supply of dialysis solution (PF, Patient Fill)

When the first valve arrangement 9 is in its second open position the tube 22 is open and connects the heat bag 8 with the catheter 13. The warm contents in the heat bag is supplied to the patient by means of gravity. Any remaining dialysis solution in the heat bag is registered with the help of the weighing device.

Draining of the discharge bag (SD, system Drain)

When the second valve arrangement 14 is in its second opened position, the tube 24 is open and connects the discharge bag 12 with the collection bag 16 and the contents in the discharge bag 12 is drained to the collection bag 16. The tube 24 can similarly be connected to a drain or waste. The collection bag 16 can consist of used supply bags 5 or a larger collection vessel, in accordance with requirements.

Figure 3:
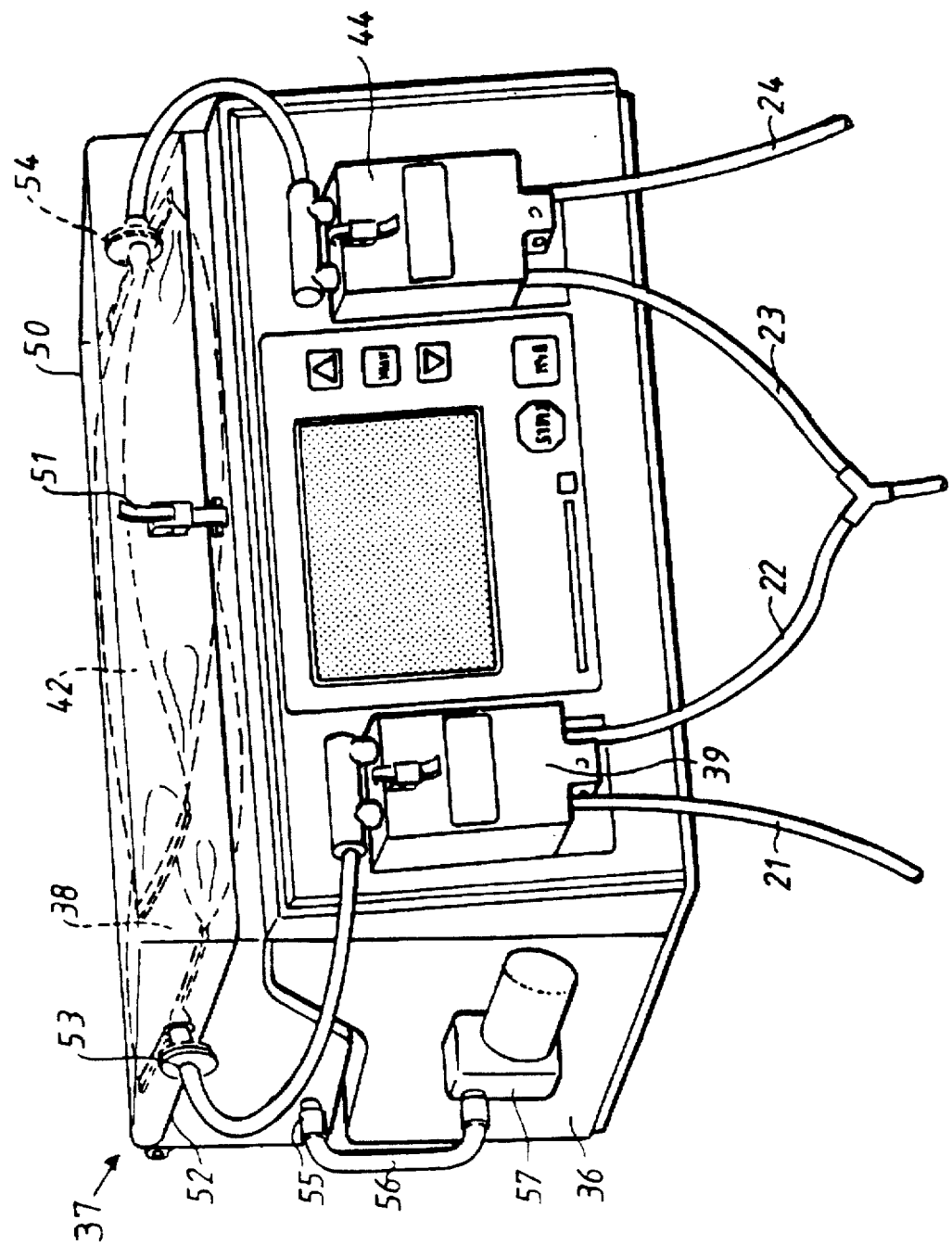
FIG. 3 is a perspective view of an apparatus according to the invention.

FIG. 3 shows an apparatus according to the present invention. The apparatus can be used with the tube-set which is shown in FIG. 2 and the supply bags and fluid containers which can be seen in FIG. 1. The components of the apparatus according to FIG. 3 which are identical or which correspond to components which are shown in the apparatus according to FIG. 1 have been given the same reference numerals as in FIG. 1 but increased by 30, i.e. the heat bag 8 according to FIG. 1 has now been given the reference numeral 38 in FIG. 3.

The difference between the apparatus according to FIG. 3 and the apparatus according to FIG. 1 is that the discharge bag 42 has been placed on top of the heat bag 38 and the second valve arrangement 44 has been attached to the regulating unit 36. Furthermore the scales 37 have been provided with a cover so that the scales and the cover together form a case which surrounds the heat bag and the discharge bag.

The apparatus according to FIG. 3 thus comprises a regulating unit 36 with a first valve arrangement 39 and a second valve arrangement 44. The first tube 21 passes through the valve arrangement 39 to a heat bag 38 positioned on the scales 37. The second tube 22 leads from the heat bag 38 through the valve arrangement 39 to a patient. The third tube 23 leads from the patient through the second valve arrangement 44 to a discharge bag 42 positioned on the scales 37. The fourth tube 24 leads from the discharge bag 42 via the second valve arrangement 44 to a waste or collection bags.

The regulating unit 36 further comprises, in accordance with the invention, a case 50 positioned above the scales 37. The case 50 tightly conforms to the appearance and form of the scales 37 such that a sealed space is formed between the case 50 and the scales 37. The case 50 is provided with locking means 51 for secure attachment of the case 50 to the scales 37. The case can be completely removable or can be foldable by means of hinges in a convenient manner. Additionally there are seals 52 between the case and the scales.

The tube from the heat bag 38 and from the discharge bag 42 passes through the wall of the case via sealed holes 53, 54. The case 50 is further provided with a connection 55 for a tube 56, which leads to a pump 57 arranged on the regulating unit 36. The pump can be positioned inside the regulating unit 36.

The function of the apparatus according to FIG. 3 is in principle the same as that described above for the GAMBRO PD 100 system. However the transport of the dialysis solution occurs by means of positive and negative pressure inside the case 50.

An example of a treatment starts with filling of heat bag (HF) by bringing a negative pressure into the case 50 by means of the pump 57 via conduit 56 and the connection 55. At the same time the tube 21 is opened by means of the valve arrangement 39 and fresh dialysis fluid flows from the supply container to the heat bag 38. When the heat bag 38 is filled by a desired amount, which is determined by weighing of the heat bag 38, the valve 39 is closed. The contents of the heat bag is heated, by means of an in-built heat element in the scales 37 (not shown in FIG. 3), to the desired temperature.

Then, the catheter in a connected patient is joined with the discharge bag 42 by placing the second valve arrangement 44 in its first open position and used dialysis fluid is extracted from the patient (PD, Patient Drain) by the application of a negative pressure in the case. The amount of extracted solution is weighed.

The catheter in the patient is then joined with the heat bag 38 by placing the first valve arrangement 39 in its second open position for supplying fresh dialysis solution (PF), by means of an overpressure in the case. When a suitable volume has been supplied to the patient, the first valve arrangement 39 is closed.

The discharge bag is finally connected with a drain or a collection bag by placing the second valve arrangement 44 in its second open position and an overpressure is applied in the case for releasing the used dialysis solution (SD).

The above described cycle can be modified in different ways according to which manner is applicable in a particular case. It is thus normally suitable if a supply to the patient (PF) follows immediately after an extraction from the patient (PD) so that the patient receives fresh dialysis solution as quickly as possible. It is also preferably if the heat bag is filled (HF) before draining of the discharge bag (SD) since the heat bag is given a sufficiently long heating time thereby. In this way the heat contents in the discharge bag can be used to heat the contents in the heat bag which reduces energy consumption.

According to a preferred embodiment of the invention it can, however, be advantageous to reverse HF and SD so that draining of the discharge bag (SD) occurs before filling of the heat bag (HF), as first described. The reason for this is that the pressure in the case then only has to be changed once during each cycle from negative pressure during filling of the heat bag and thereafter immediately following extraction of the used dialysis solution from the patient to positive pressure for supplying fresh dialysis solution to the patient (PF), upon which the contents in the discharge bag is drained (SD). In this way a smaller amount of pressure medium is consumed which leads to lower energy consumption. Additionally, pumps with lower capacity can be used which have a lower noise level.

It is also possible to use the apparatus according to the invention in such a way that extraction of the dialysis solution from the patient (PD) occurs with the help of gravity, as in the earlier known GAMBRO PD 100 system. For this, one uses a discharge bag 12 hung on a hook by means of a carrier arrangement as in the earlier known GAMBRO PD 100 system. Supply of fresh dialysis solution (PF) occurs however with the help of overpressure on the heat bag. In this embodiment only an overpressure on the heat bag is required, whereby the case can of course be flexible and consist of a bellows arrangement. The pressure can also be exerted by some type of mechanical arrangement such as springs or weights etc.

Figure 4:
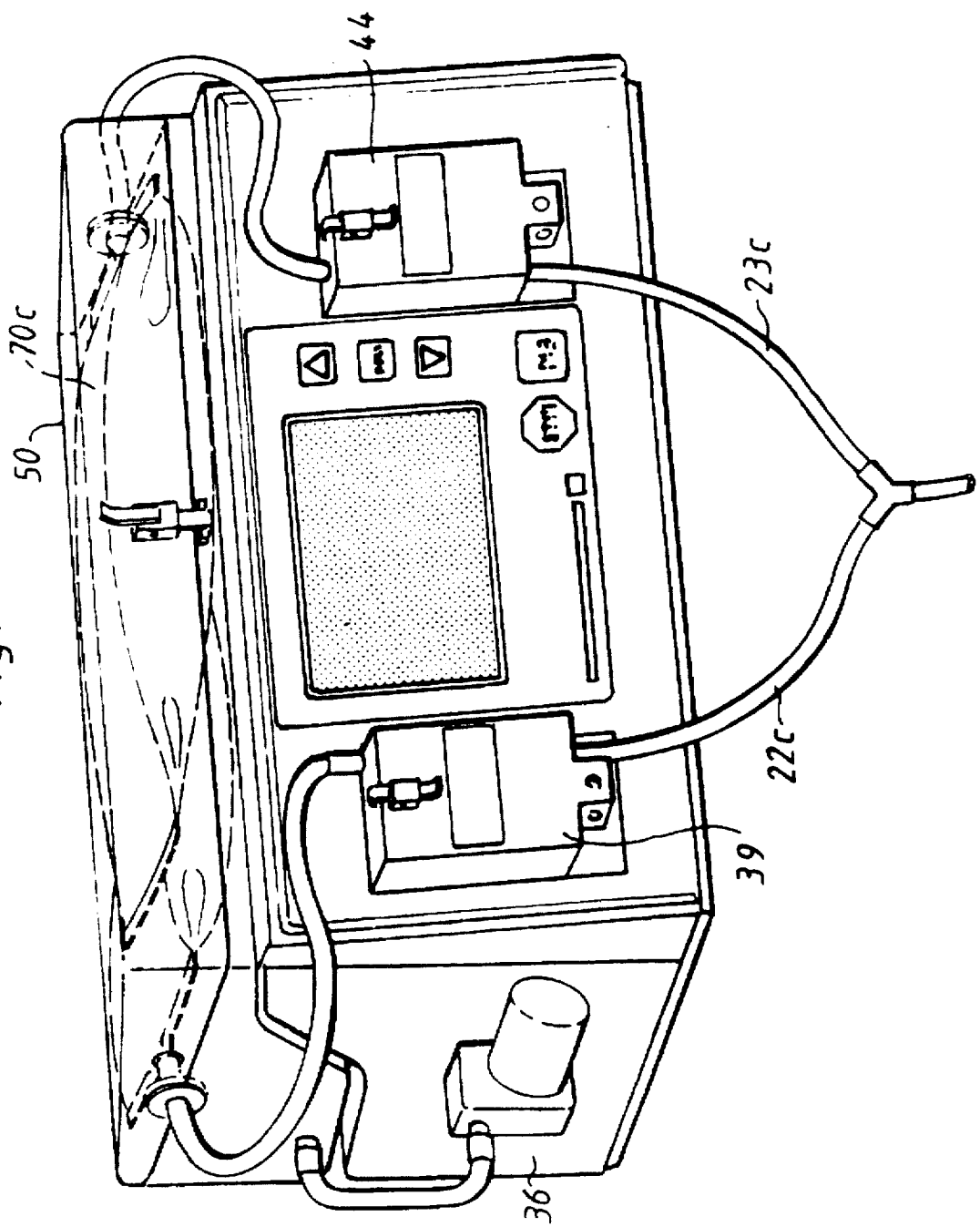
FIG. 4 is a view similar to that in FIG. 3 of an alternative apparatus according to the invention.

In an alternative embodiment of the present invention as shown in FIG. 4, the heat bag 38 and the discharge bag 42 are replaced by a ready-prepared double supply bag which is placed inside the case 50. After heating, the contents in the supply bag 5 is emptied directly to the patient by exerting an overpressure in the case 50. In this embodiment neither the first tube 21 nor the fourth tube 24 are required. The supply bag does not need to be emptied completely with each cycle but smaller amounts can be taken out during each cycle (tidal). Neither does the drain part of the bag need to be filled during each cycle but can accumulate increasing amounts for each cycle until it is full. For example the bag can contain 4,5 liters of fresh dialysis solution from the start and no used dialysis solution and then can be emptied in small amounts during each cycle, whereby the used dialysis solution goes into the thus successively increasing discharge portion of the bag. When all of the fresh dialysis solution has been used, the case 50 is opened whereupon the old supply bag is discarded and a new supply bag is applied to the apparatus in accordance with the invention.

Figure 5:
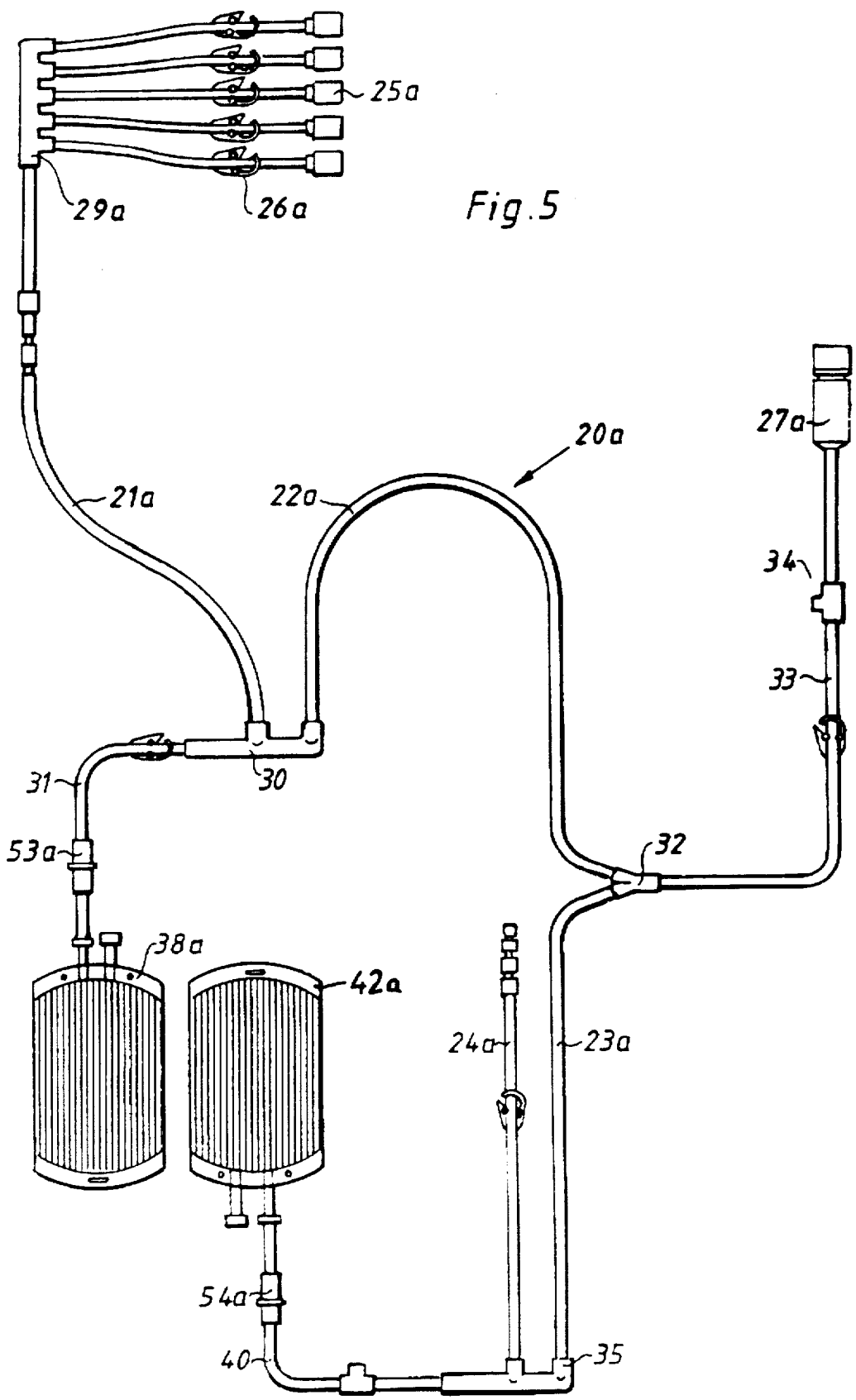
FIG. 5 is a side view of a tube-set for use with the apparatus according to the present invention.

FIG. 5 shows a tube-set intended for use together with the apparatus according to FIG. 3. The components of the tube-set according to FIG. 5 which are identical with, or correspond to, the components which are shown in FIG. 2 have been given the same reference numerals but with the addition of "a". Thus the tube-set 20a according to FIG. 5 comprises connectors 25a to supply bags as well as tube clamps 26a. Tubes from the connectors 25a are coupled together with a branch coupling 29a, which leads to the first tube 21a. The first tube 21a and the second tube 22a are joined to each other by an F-coupling 30. The F-coupling is connected with the heat bag 38a via a tube 31 provided with a tube clamp. The tube 31 passes into a bushing 53a corresponding to the hole 53 of FIG. 3. The second tube 22a and the third tube 23a are connected to each other by a Y-coupling 32 which is connected via a tube 33 to a connector 27a to a catheter. The tube 33 is provided with an optional inlet 34 for an infusion fluid. The third tube 23a is connected with a fourth tube 24a leading to the waste via an F-coupling 35, which furthermore is connected with the discharge bag 42a via a tube 40 provided with a bushing 54a corresponding to the hole 54 of FIG. 3. The tube-set 20a is provided with a plurality of colour codings in order to simplify the connection, as is known.

Figure 6:
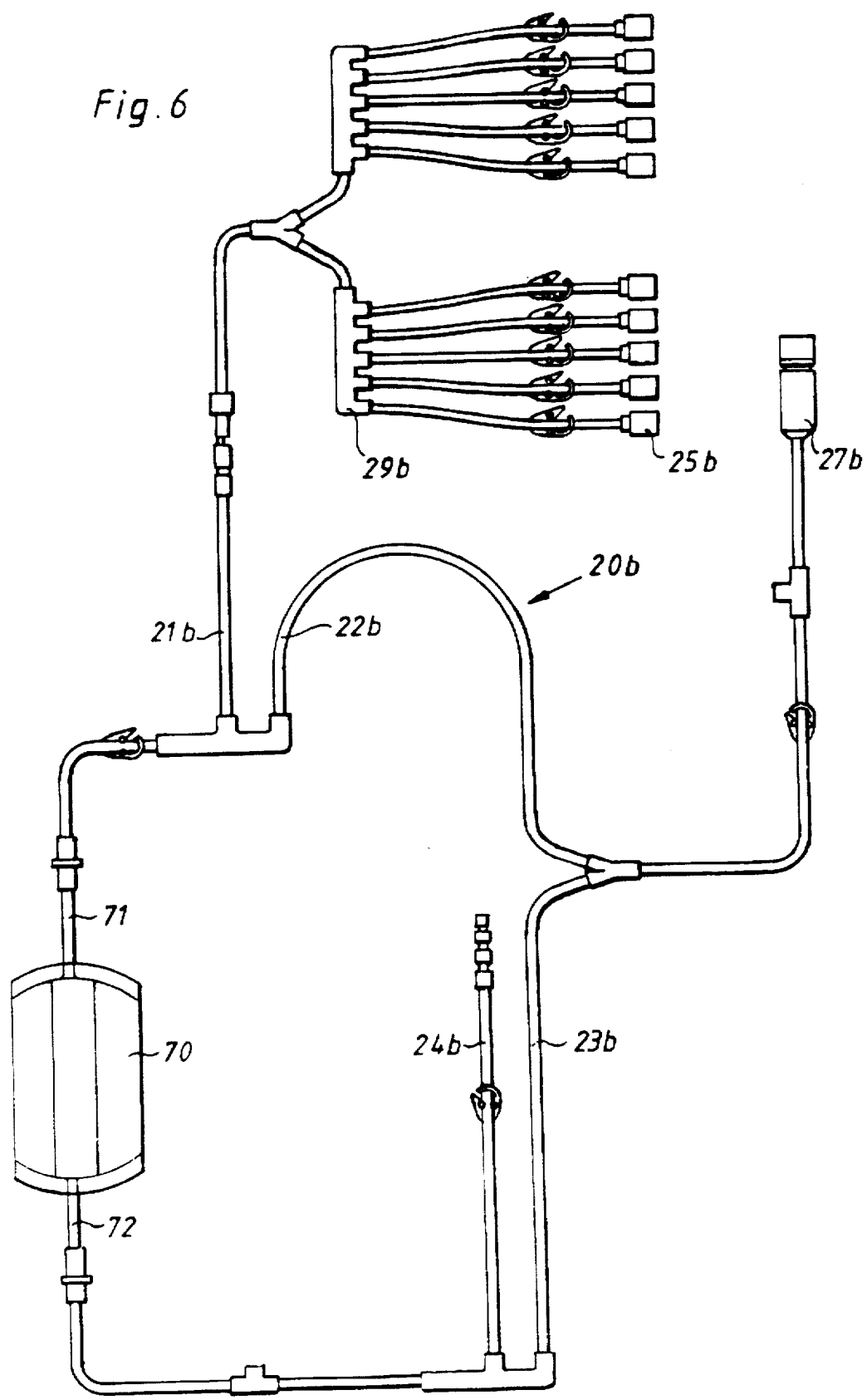
FIG. 6 is a side view of an alternative tube-set.

FIG. 6 shows a tube-set 20b similar to the tube-set 20a according to FIG. 5 whereby the same components have been given the suffix "b". The difference with respect to FIG. 5 is that the heat bag and the discharge bag have been combined as a single double bag 70. The double bag 70 has a first conduit 71 connected with a first chamber of the double bag 70 and a second connection 72 connected with a second chamber of the double bag 70. Additionally, connectors 25b are provided for ten supply bags. The function is clear from the above description of FIGS. 3 and 5.

Figure 7:
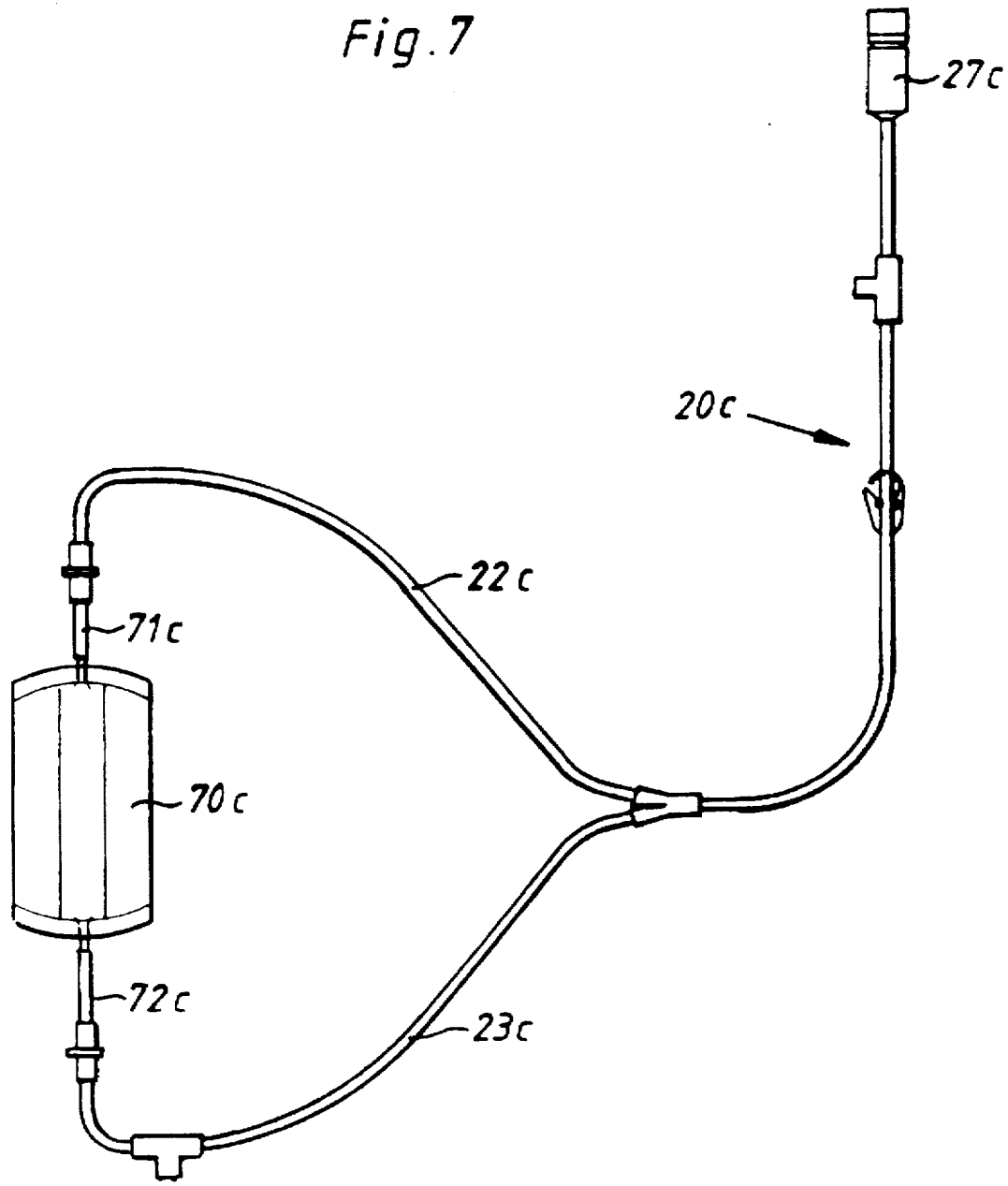
FIG. 7 is a side view of a simplified tube-set.

FIG. 7 shows a third tube-set 20c, particularly adapted for use together with the alternative embodiment of the apparatus according to FIG. 4, whereby the same components as in FIGS. 5 and 6 have been given the addition "c". A double bag 70c corresponding to the double bag 70 according to FIG. 6 and provided with two connections 71c and 72c is used. The connections are joined with the second tube 22c and the third tube 23c respectively which, via a Y-coupling, lead to a connector 27c to the patient's catheter. The tube-set according to FIG. 7 is very simple and cheap to manufacture.

If the connection 71c and the connection 72c are on the same side of the bag, the bushings 53c, 54c can be combined into a common bushing which reduces the risk of leakage during operation of the apparatus. Additionally double-lumen tubes can be used as described in EP-A1-499 718. In this way the tube-set can be additionally simplified.

FIG. 3 shows a pump 57 for supplying air to the inside of the case 50. The pump 57 is arranged to provide a positive or negative pressure within the range −0.3 bar to +0.3 bar. The pressure which the pump is able to achieve is defined by the construction of the pump and the rotational speed. Suitable values of the rotational speed can be stored in the memory of the regulating unit 36.

It is clear that different pressures can be used for the four different cycles. During filling of the heat bag from the supply bags, it is desirable that filling occurs quickly, for which reason an underpressure of e.g. −0.3 bar can be used. The filling is continually monitored by the weighing device. When a predetermined amount has entered the heat bag, the filling is stopped.

Supply of fresh dialysis solution to the patient (PF) should occur as quickly as possible, however without subjecting the patient to discomfort. A suitable overpressure in the case can be about 0.1 bar. The supply pressure can be larger at the start of supplying and then reduce towards the end of supplying. The supply flow is continually monitored by means of the weight reduction of the heat bag. If any abnormal conditions occur, the apparatus can stop the supply. For example pressure during supply can be high, without any supply occurring, which indicates that the catheter is blocked. Suitable relationships between the supply pressure and the flow can be programmed into the memory of the apparatus.

Extraction of used dialysis fluid from the patient (PD) occurs with a moderate underpressure of somewhere around −0.05 bar. The extraction of the dialysis solution from the patient is also monitored continually with the weighing device for checking a suitable relationship between the extraction pressure and flow. If abnormal conditions are present, the extraction is stopped. The relationship between the extraction pressure and flow can be programmed into the memory of the apparatus.

Draining of used dialysis solution from the extraction bag (SD) occurs at a relatively high pressure of e.g. 0.3 bar so that extraction occurs as quickly as possible.

Preferred supply pressure and extraction pressure as well as flow speeds can already be programmed in a separate memory positioned on a so-called smart card which is specifically for the patient. This smart card additionally comprises other parameters in order to operate the apparatus according to the invention depending on the specific requirements of the patient. The card is programmed by the patient's doctor or dialysis nurse in accordance with his prescription and is entered into the apparatus for use. The programming can occur in connection with some type of evaluation system for PD-dialysis, such as GAMBRO evaluation computer program, Patient Dialysis Capacity, PDC.

The pump 57 is suitably a centrifugal pump which achieves a suitable output pressure of e.g. maximum 0.3 bar. By regulating the cyclic speed and the rotational direction of the pump, the pressure which is supplied to the case can be varied between −0.3 bar and +0.3 bar relative to the surrounding atmosphere. By reversing the rotational direction a negative pressure is obtained.

Figure 8:
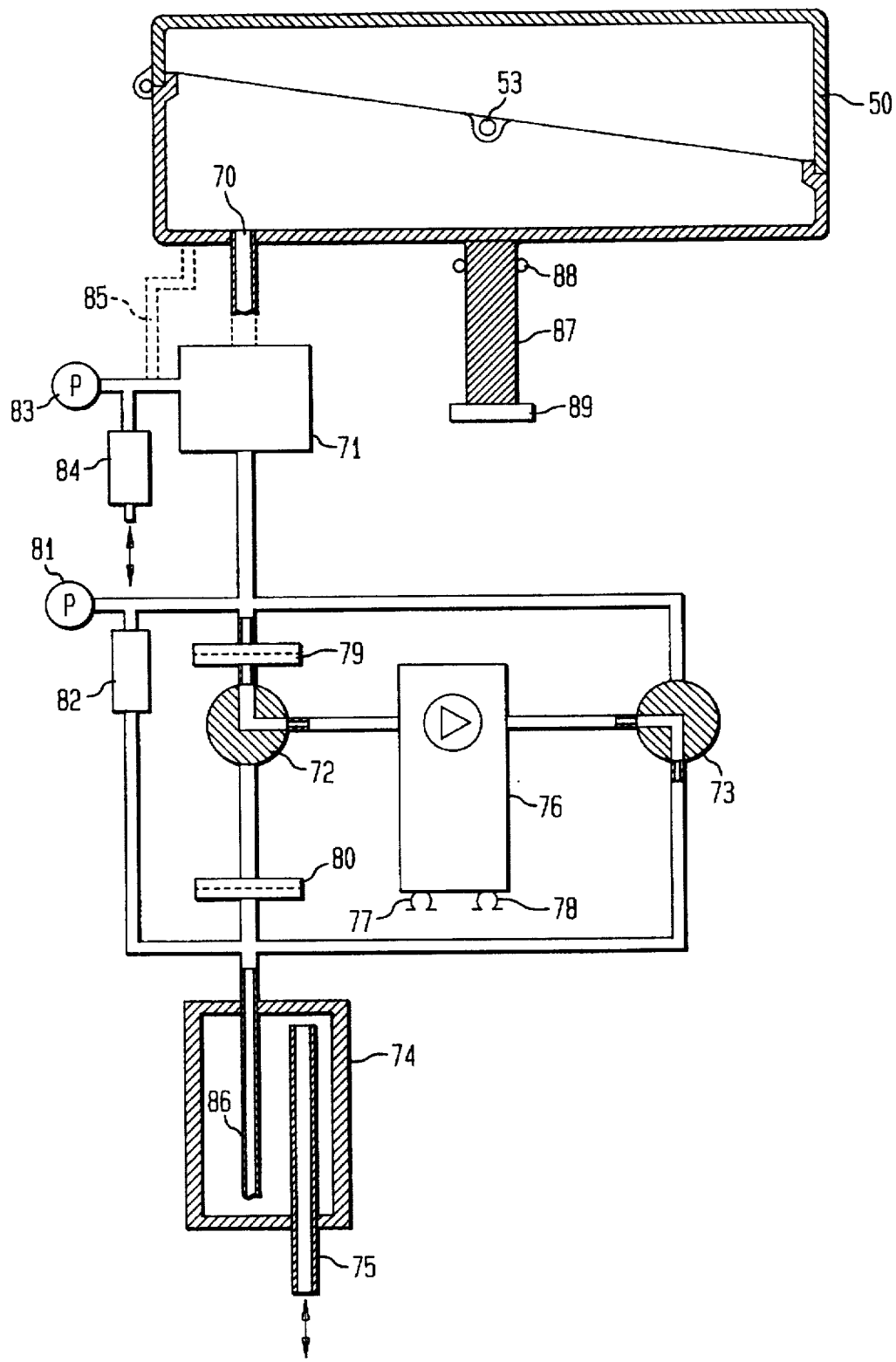
FIG. 8 is a schematic view of a preferred pump arrangement for the apparatus according to the invention.

Alternatively, the change of the direction of pressure (positive or negative pressure relative to the surrounding atmosphere) can occur by means of valve arrangement, as shown in FIG. 8.

In the first and preferred embodiment of the pump arrangement, the case 50 is provided with a second opening 70, in addition to holes 53,54. Opening 70 is connected to a damping volume 71 having a sufficient volume for damping any pressure surges occuring during valve or pump operation. Damping chamber 71 is connected to two valves 72,73 and further to a muffler 74 being connected to the atmosphere via a tube 75.

Interposed between valves 72,73 is a pump 76, preferably a membrane pump, although any suitable pump, which achieves a sufficent output pressure, can be used, provided it is sufficently silent. The pump 76 is connected to the chassi of the apparatus via dampening springs 77,78 shown as rubber spring elements of an omega shape. The spring members dampen any transmission of structural vibrations from the pump to the apparatus. Any sound passing from the pump to the surroundings via the tubes must pass the muffler 74, which dampens such sound or vibrations.

Particle filters 79,80 are inserted in the tubes in a suitable position for preventing particles from entering pump 76. A suitable filter size is about 40 microns.

Valves 72 and 73 are operated for connecting pump 76 for positive or negative pressure in the case. In FIG. 8 are shown the positions for negative pressure for filling the heater bag 38 with fresh solution. By reversing the direction of valves 72 and 73, the opposite operation takes place.

The correct operation of the pump system is monitored by a pressure sensor 81. Sensor 81 is connected to a microcomputer controlling the overall apparatus, specifically valves 72,73 and pump 76. The rotational speed of pump 76 is controlled in order to obtain a desired positive or negative pressure, monitored by pressure sensor 81. A bleeding valve 82 is connected in a shunt line, connecting the case 50 with the atmosphere via tube 75 in certain occasions. Bleed valve 82 is normally open if not activated by an electric current.

The pump arrangement is also provided with a protective system shown as a pressure sensor 83 and a bleed valve 84 connecting damping chamber 71 with the atmosphere at fault conditions. The protective system can, if desired, be connected directly to case 50 via a tube 85, (shown by dashed lines in FIG. 8).

Muffler 74 is shown as a cylindric vessel provided with an inlet tube 75 and an outlet tube 86. Muffler 74 has thick walls and is made of a plastic material. Since the air must pass a long distance inside muffler 74, sound is damped and absorbed. Any type of muffler or silencer can be used.

Case 50 is supported by a single shaft 87 guided by bearings 88 and moveable in the verticle direction. The lower end of the shaft 87 is supported by a load cell 89, emitting an electric signal, the size of which is dependent of the pressure exerted by shaft 87 on the upper side of load cell 89. This technique is well known.

Figure 9:
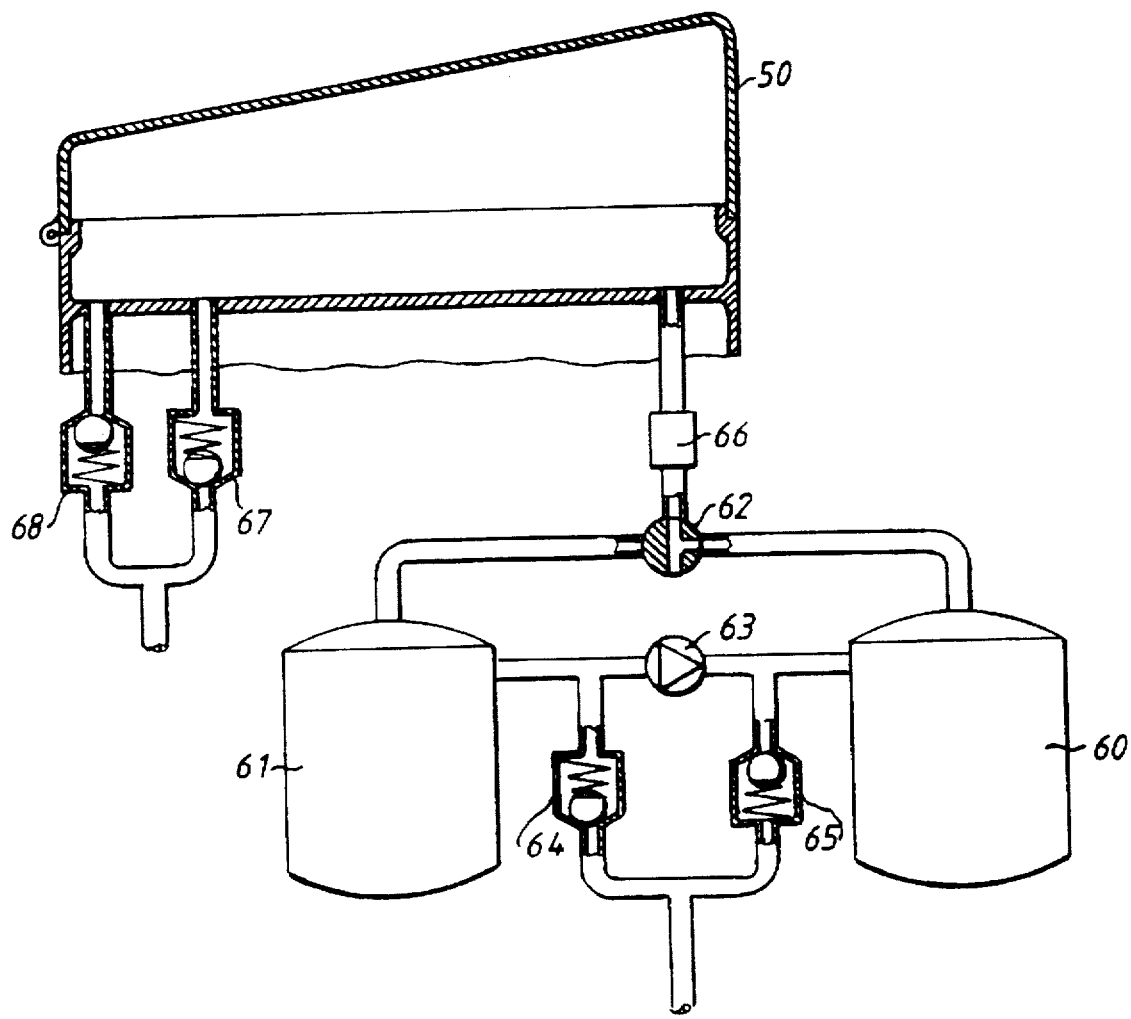
FIG. 9 is a schematic view of a second pump arrangement for the apparatus according to the invention.

In a second embodiment of the pump arrangement as shown in FIG. 9, another arrangement is used to achieve positive and negative pressure in the case. The pump arrangement comprises two pressure chambers 60, 61, in which overpressure and underpressure respectively prevail. The pressure chambers are connected selectively with the case according to the desired functional scheme by means of a three-way valve 62. The volume and the pressure in the pressure chambers are dimensioned so that a complete cycle can be performed. For example the overpressure can be about 2 bar and the underpressure about −0.9 bar relative to atmosphere. In this way the pressure chambers have a combined volume which is about 5 liters, but still at least a complete cycle can be carried out with the contents in these pressure chambers without the help of a pump. In this way it can be ensured that the apparatus can operate during a longer period in the event of a power break and can be operated with only in-built batteries and a minimum of power consumption, i.e. the pump does not need to be operated.

A pump 63 is arranged between the pressure chambers 60 and 61 in order to form and maintain the pressure in these chambers. The pump can be dimensioned for continual operation and has a large amount of time in order to build up the necessary pressure between the cycles for PD-treatment. Thus a pump can be used which is practically silent. The pump can be started a suitable time before an exchange is to take place, for example 20 minutes before. During 20 minutes, the pump builds up the necessary pressures inside chambers 60,61. The volumes and pressures of chambers 60,61 are sufficent for performing the operation without any net flow from the pump. However, the pump is still operated for increasing the available amount of air and pressure. In this way, a very small and silent pump can be used.

The pressure regulation valves 64, 65 connect the input side and the output side respectively of the pump to atmosphere. The pressure regulation valves are adjusted to the aforementioned exemplifying values of −0.9 bar and 2 bar so that these pressures are obtained as the pump works.

For reasons of safety the case is provided with pressure relief valves 67, 68 which ensure that the case can not be pressurized with too large a pressure.

A pressure sensor 66 is positioned in the conduit to the case and gives a pressure signal to a microcomputer which regulates the function of the apparatus and particularly the valve 62 which comprises pressure reduction arrangements to regulate the pressure which is supplied from the pressure chambers to the case.

Even if a gas, particularly air, is preferred as the pressure medium it is also possible to use fluids such as water. It is then important that the case 50 is completely airtight since suction of air during underpressure in the case would disturb the operation.

The upper part of the case can be transparent so that the function of the apparatus can be observed from the outside. In this way it can be determined whether the bags have become blocked in some way or whether other types of risk for incorrect operation are present, which increases the safety of the apparatus.

It is also possible to exert pressure on the bags 38 and 42 by means of some mechanical arrangement such as lever arms, springs and/or weights.

Since the heat bag 38 as well as the collection bag 42 are positioned on the same scales, the advantage is obtained that the same measurement cell measures the contents of both bags which reduces possible measurement errors.

Additional safety devices can be used on the tube-set in order to ensure that the patient is not subjected to too high a pressure, such as hydrophobic filter arrangements, pressure boxes with micro-switches etc. Such devices are already known in the art and can be used by a skilled man.

We claim:

1. An apparatus for conducting peritoneal dialysis comprising at least one flexible container for handling a fluid useful in said peritoneal dialysis, supply means for supplying said fluid to said at least one flexible container, weighing means for weighing the contents of said at least one flexible container, a conduit connected to said at least one flexible container for conducting a flow of said fluid, enclosure means surrounding said at least one flexible container thereby forming a space between said at least one flexible container and said enclosure means, and pressure control means for altering the pressure within said space for transferring said fluid from said at least one flexible container through said conduit.

2. The apparatus of claim 1, wherein said enclosure means includes an entry port for permitting said conduit to pass through said enclosure means.

3. The apparatus of claim 2, wherein said entry port includes entry port sealing means for sealing said entry port with respect to said conduit.

4. The apparatus of claim 1, wherein said pressure control means comprises pressure increasing means for creating a pressure greater than atmospheric pressure within said space for emptying said fluid from said at least one flexible container through said conduit.

5. The apparatus of claim 1, wherein said enclosure means is rigid, and wherein said pressure control means comprises pressure decreasing means for creating a pressure less than atmospheric pressure within said space for driving said fluid into said at least one flexible container through said conduit.

6. The apparatus of claim 4 or 5 wherein said space includes a pressure medium comprising a gas.

7. The apparatus of claim 6, wherein said gas comprises air.

8. The apparatus of claim 4 or 5, wherein said space includes a pressure medium comprising a liquid.

9. The apparatus of claim 8, wherein said liquid comprises water.

10. The apparatus of claim 1, wherein said enclosure means comprises a cover movable between an open and a closed position, and including sealing means for sealing said cover when in said closed position.

11. The apparatus of claim 1, wherein said at least one flexible container comprises first and second flexible containers, wherein said conduit comprises a first conduit for connection to said first flexible container, and including a second conduit connected to said second flexible container for conducting a flow of fluid.

12. The apparatus of claim 11, wherein said first flexible container is adapted for handling a fresh fluid, and said second flexible container is adapted for handling a used fluid.

13. The apparatus of claim 1, including valve means associated with said conduit for controlling the flow of said fluid in said conduit.

14. The apparatus of claim 1, wherein said at least one flexible container comprises a plastic bag.

15. The apparatus of claim 1, wherein said space includes a pressure medium, and wherein said pressure control means includes a pump for controlling the flow of said pressure medium into and out of said space.

16. The apparatus of claim 15, including damping means for damping vibrational movements created by said pump.

17. The apparatus of claim 16, including muffler means for reducing the sound level of said pump.

18. The apparatus of claim 15, wherein said pump has an output pressure which is dependent upon the cycle speed thereof.

19. The apparatus of claim 18, wherein said pump comprises a centrifugal pump.

20. The apparatus of claim 1, wherein said pressure control means comprises a first pressure chamber including a gas maintained at a pressure greater than atmospheric pressure and a second pressure chamber including a gas maintained at a pressure less than atmospheric pressure, and valve means for selectively connecting said first and second pressure chambers with said enclosure means.

21. The apparatus of claim 20, wherein said pressure control means includes a pressure sensor for controlling said valve means.

22. The apparatus of claim 20, wherein said pressure control means includes a pump in communication with said first and second pressure chambers for increasing the pressure in said first pressure chamber and decreasing the pressure in said second pressure chamber, first pressure chamber valve means for regulating the pressure in said first pressure chamber and second pressure chamber valve means for regulating the pressure in said second pressure chamber.

23. The apparatus of claim 22, wherein said pump operates substantially continuously.

24. The apparatus of claim 20, including pressure relief means for maintaining the pressure within said enclosure means between predetermined limits.

25. The apparatus of claim 24, wherein said predetermined limits are between about 0.3 bar and −0.3 bar.

* * * * *

UNITED STATES PATENT AND TRADEMARK OFFICE
CERTIFICATE OF CORRECTION

PATENT NO. : 5,722,947
DATED : March 3, 1998
INVENTOR(S) : Jeppsson et al.

It is certified that error appears in the above-identified patent and that said Letters Patent is hereby corrected as shown below:

Delete columns 1-14 and substitute the attached columns 1-14.

The title page, showing illustrative figure should be deleteed and substitute therefor the attached title page.

Signed and Sealed this

Twenty-fourth Day of November,1998

Attest:

BRUCE LEHMAN

Attesting Officer

Commissioner of Patents and Trademarks

United States Patent
Jeppsson et al.

[11] Patent Number: 5,722,947
[45] Date of Patent: Mar. 3, 1998

[54] APPARATUS FOR CARRYING OUT PERITONEAL DIALYSES

[75] Inventors: Jan-Bertil Jeppsson, Lomma; Tor Nordlie, Eslov, both of Sweden

[73] Assignee: Gambro AB, Sweden

[21] Appl. No.: 687,596

[22] PCT Filed: Jan. 30, 1995

[86] PCT No.: PCT/SE95/00086
§ 371 Date: Sep. 17, 1996
§ 102(e) Date: Sep. 17, 1996

[87] PCT Pub. No.: WO95/20985
PCT Pub. Date: Aug. 10, 1995

[30] Foreign Application Priority Data

Feb. 3, 1994 [SE] Sweden ............... 9400347

[51] Int. Cl.⁶ ............................... A61M 1/00
[52] U.S. Cl. .................... 604/29; 128/DIG. 12; 128/DIG. 13; 604/67
[58] Field of Search .................. 664/29, 65–67, 664/30–34, 49–53

[56] References Cited

U.S. PATENT DOCUMENTS 4,412,917 11/1983 Ahjopalo.
4,413,988 11/1983 Handt et al..

*Primary Examiner*—Michael Buiz
*Assistant Examiner*—Manuel Mendez
*Attorney, Agent, or Firm*—Lerner, David, Littenberg, Krumholz & Mentlik

[57] ABSTRACT

An apparatus for conducting peritoneal dialysis is disclosed including a flexible container for handling of dialysis fluid, a tube for supplying the fluid to the flexible container, a scale for weighing the contents of the flexible container, a conduit for conducting a flow of the fluid with respect to the flexible container, a case surrounding the flexible container, and a pump or valve system for altering the pressure within the case in order to transfer the fluid from the flexible container to the conduit.

25 Claims, 9 Drawing Sheets

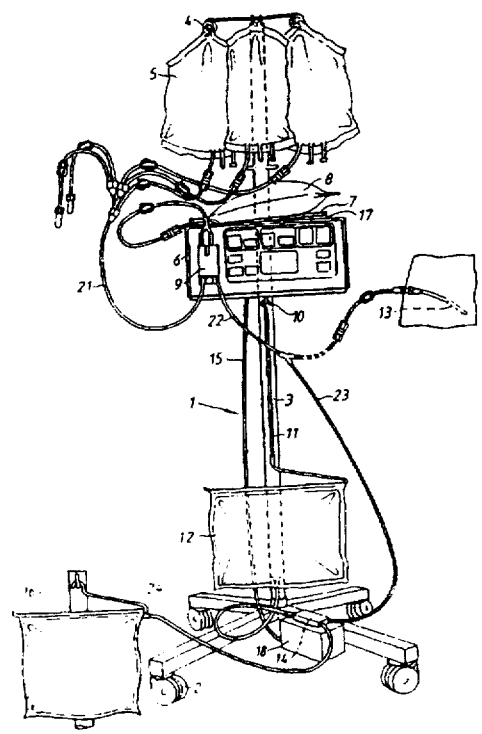
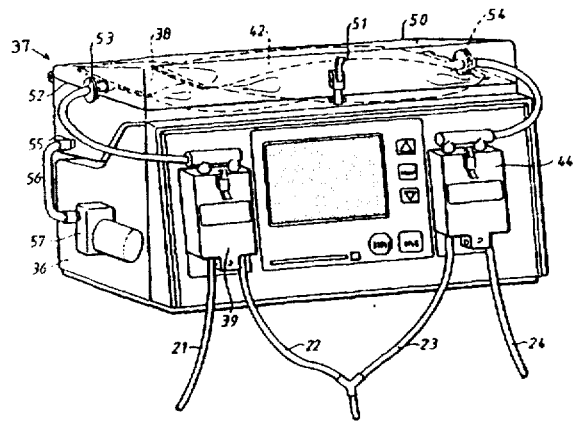

APPARATUS FOR CARRYING OUT PERITONEAL DIALYSIS

FIELD OF THE INVENTION

The present invention relates to an apparatus for administering peritoneal dialysis solution to a patient, such apparatus being known as a PD-cycler.

BACKGROUND OF THE INVENTION

The present invention can best be understood against the backdrop of the technology which is used by the applicant in the commercial GAMBRO PD 100 system. This system comprises of a stand which is about 2 meters high. At a first upper level, at the upper end of the stand, there are hooks for hanging bags containing ready-mixed supply solution for peritoneal dialysis. The supply bags are connected by tubes to a heat bag positioned just below the supply bags at a second intermediate level. The heat bag is positioned on a heating surface of a weighing device.

The heat bag is filled, under the control of valves from the supply bags, and may have a volume of about 2 liters or slightly more. When the contents in the heat bag have reached the correct temperature, they are fed by gravity to a catheter terminating in the abdominal cavity of the patient. The catheter and the abdominal cavity are at a third level, which is below the second level.

When the dialysis solution has fulfilled its task it is drained to a discharge bag positioned on a fourth level. The discharge bag is attached to a hook arrangement, which hangs from the weighing device for the heat bag. In this manner, the same weight measuring element or load cell is used for weighing the heat bag as well as the discharge bag. The contents of the discharge bag are finally drained either directly to a drain or to collection bags which are situated on a fifth and lowest level. All transport of solution occurs by means of gravity between the five different levels. It is therefore obviously important that the patient be situated at a particular level below the heat bag and above the discharge bag.

A tube-set intended for use in the GAMBRO PD 100 system is shown in European Patent No. A1-499 718.

A similar cycler system is described in U.S. Pat. No. 5,141,492, in which only three levels are used. In this case, the input amount is not weighed but only determined by the size of the supply bags. The supply bags are heated directly to the appropriate temperature. The discharge bag is also used for collection and is dimensioned to be sufficiently large. On the collection bag is weighed.

In order to avoid dependence on gravity for feeding the dialysis solution it has been suggested that pump arrangements be used for this purpose. Such a pump arrangement is disclosed in U.S. Pat. No. 4,412,917 in the form of a peristaltic pump for feeding dialysis solution to a patient from a supply container positioned at floor level. A pressure monitoring arrangement insures that the pressure to the catheter does not exceed a predetermined value. The supply container as well as the collection container are positioned on a weighing device for monitoring the inlet and outlet of dialysis solution to and from the patient.

U.S. Pat. No. 4,560,472 discloses a pump arrangement for pumping supply solution from a first level to a heat bag positioned at a higher level. The continued transport of the dialysis solution occurs thereafter by means of gravity. In this manner, the need to lift the heavy supply bags up to a high level is avoided.

U.S. Pat. No. 5,004,459 discloses an even more automated system for administering PD-solution. This apparatus includes a separate filling pump for filling the abdominal cavity and a separate outlet pump for extraction from the abdominal cavity. Two pressure and/or flow sensors detect and limit the pressure and/or flow for the supply and extraction. The apparatus further comprises mixing of dialysis concentrates with pure water, possibly with the addition of glucose.

U.S. Pat. No. 4,311,587 discloses a supply arrangement for dialysis solution through a sterile filter. The object in this case is to avoid peritonitis by filtering the incoming solution. Since the sterile filter implies a large flow resistance, a higher pressure is required than that which can practically be achieved by means of gravity. Thus, a bag containing dialysis solution is placed in a belt under the arm and manual pressure is applied with the arm or elbow to the bag in order to press the dialysis solution through the sterile filter and through the catheter into the abdominal cavity. Extraction occurs with the help of gravity. One-way valves are used in this construction.

U.S. Pat. No. 5,141,493 discloses a system in which a pump and a pressure sensor are used for supplying and extracting a dialysis solution to and from a patient. The dialysis solution is then circulated in a primary circuit through a dialyser which in turn is connected with a secondary circuit, whereby the dialysis solution in the first circuit is cleaned with the help of said dialyser.

International Patent No. 90/13795 discloses a pump arrangement intended, among other things, for use in connection with peritoneal dialysis. The pump arrangement consists of a chamber divided by an elastic membrane. On one side of the membrane is the solution which is to be pumped and on the other side of the membrane there is a gas. Positive and negative pressure is supplied to the chamber with the gas. The pumped volume is monitored and measured by measuring the gas volume in the chamber for gas.

European Patent No. 94,682 discloses a device for reinfusion of blood, comprising a vessel having rigid walls enclosing a flexible container. Blood is fed into the flexible container by exerting a subpressure in the space between the container and the vessel. The blood is then reinfused by exerting an overpressure in the space between the container and the vessel.

SUMMARY OF THE INVENTION

A first object of the present invention is to provide an apparatus for peritoneal dialysis where the supply and/or extraction of the dialysis solution to and/or from the patient occurs entirely or partly without the help of gravity, i.e., with the help of pump arrangements. In this way it is possible for the patient to adopt different positions with respect to the apparatus without affecting the function of the apparatus. Additionally, higher pressure can be used than that which is practically possible with supply by means of gravity, which reduces the supply and extraction times. At the same time, the flow rates can be adapted to the demands of a specific patient.

A second object of the present invention is to provide such a pump arrangement which is safe and convenient to use and which is sufficient silent for night operation.

A further object of the present invention is to simplify the tube-set which is required for operating the apparatus for peritoneal dialysis.

It is desirable to obtain a pump function without the use of a pump which will be contaminated by dialysis solution. The obvious choice is, for example, a peristaltic pump (as shown in U.S. Pat. No. 4,412,917), which influences the tubes in the system without itself becoming contaminated.

In accordance with the present invention, these and other objects have now been realized by the discovery of an apparatus for conducting peritoneal dialysis which comprises at least one flexible container for handling of fluid useful in peritoneal dialysis, supply means for supplying the fluid to the at least one flexible container, weighing means for weighing the contents of the at least one flexible container, a conduit connected to the at least one flexible container for conducting a flow of the fluid, enclosure means surrounding the at least one flexible container thereby forming a space between the at least one flexible container in the enclosure means, and pressure control means for altering the pressure within the space for transferring the fluid from the at least one flexible container through the conduit.

In accordance with one embodiment of the apparatus of the present invention, the enclosure means includes an entry port for permitting the conduit to pass through the enclosure means.

In accordance with another embodiment of the apparatus of the present invention, the pressure control means comprises pressure increasing means for creating a pressure greater than atmospheric pressure within the space for emptying the fluid from the at least one flexible container through the conduit. In another embodiment, the enclosure means is rigid, and the pressure control means comprises pressure decreasing means for creating a pressure less than atmospheric pressure within the space for driving the fluid into the at least one flexible container through the conduit. Preferably, the space includes a pressure medium comprising a gas, such as air, or a liquid, such as water.

In accordance with another embodiment of the apparatus of the present invention, the enclosure means comprises a cover removable between an open and closed position, and including sealing means for sealing the cover when it is in the closed position.

In accordance with another embodiment of the apparatus of the present invention, the entry port includes entry port sealing means for sealing the entry port with respect to the conduit.

In accordance with another embodiment of the apparatus of the present invention, the at least one flexible container comprises first and second flexible containers, wherein the conduit comprises a first conduit for connection to the first flexible container, and including a second conduit connected to the second flexible container for conducting a flow of fluid. Preferably, the first flexible container is adapted for handling a fresh fluid and the second flexible container is adapted for handling a used fluid.

In accordance with another embodiment of the apparatus of the present invention, the apparatus includes valve means associated with the conduit for controlling the flow of the fluid in the conduit. In a preferred embodiment, the at least one flexible container comprises a plastic bag.

In accordance with another embodiment of the apparatus of the present invention, the space includes a pressure medium and the pressure control means includes a pump for controlling the flow of the pressure medium into and out of the space. Preferably the pump has an output pressure which is dependent upon the cycle speed, such as a centrifugal pump.

In accordance with another embodiment of the apparatus of the present invention, the pressure control means comprises a first pressure chamber including a gas maintained at a pressure greater than atmospheric pressure and a second pressure chamber including a gas maintained at a pressure less than atmospheric pressure, and valve means for selectively connecting the first and second pressure chambers with the enclosure means. Preferably the pressure control means includes a pressure sensor for controlling the valve means. In a preferred embodiment, the pressure control means includes a pump in communication with the first and second pressure chambers for increasing the pressure in the first pressure chamber and decreasing the pressure in the second pressure chamber, first pressure chamber valve means for regulating the pressure in the first pressure chamber and second pressure chamber valve means for regulating the pressure in the second pressure chamber. Preferably the pump operates it substantially continuously. In another embodiment, the apparatus includes pressure release means for maintaining the pressure within the enclosure means between predetermined limits, such as between about 0.3 bar and −0.3 bar.

In another embodiment of the apparatus of the present invention includes damping means for damping vibrational movements created by the pump. In a preferred embodiment of the apparatus also includes muffler means for reducing the sound level of the pump.

In accordance with the present invention, it is noted that the dialysis solution passes through and is heated by the heat bag in the earlier known PD 100 system. According to the present invention, such heat bag is used as a part of a pump arrangement by subjecting the heat bag to overpressure and/or underpressure. The flow to and from the heat bag is monitored continually by means of the weighing device.

The present invention thus relates to an apparatus for carrying out peritoneal dialysis comprising a weighing device adapted for weighing the contents in a first flexible container, such as the heat bag, which is connected to at least one conduit as an outlet and possibly even as an inlet for a solution from the container. According to the invention the apparatus comprises a case which is arranged to surround the container so that a space is formed between the case and the container, whereby the container includes an introduction device for introducing the conduit through the casing. The apparatus further comprises a pressure device arranged to exert a pressure eon the container for emptying thereof.

The present apparatus suitably comprises an arrangement for supplying a pressure medium under overpressure to the space between the case and the container, said space being closed. The case is preferably rigid.

The pressure medium is suitably a gas such as air, but can also be a fluid such as water. The case can consist of a lower part and an upper part. The lower part forms a weighing scale and is connected to the weighing device. The upper part can be folded away or removed from the lower part, the parts normally being sealed relative to one another. The case is connected to a pump arrangement in order to pump pressure medium in and/or out of the space between the case and the container.

The case can also comprise a second flexible container provided with a conduit for the inlet and/or outlet of a used or spent solution, whereby the first container is intended for fresh solution. Additionally, there are valve arrangements for controlling the flow of solution to and from the containers, which are suitably plastic bags.

The pump arrangement can be of the centrifugal pump type which achieves a predetermined pressure at its outlet and is reversed in order to achieve said underpressure. Alternatively, the pump can be a membrane pump controlled by a pressure sensor. In another alternative, two pressure chambers can be used for underpressure and overpressure, whereby the volume of the case is successively connected with respective pressure chambers. A pump can work more or less continually and build up the pressure in the pressure chambers. A pressure monitoring device is used to monitor and regulate the pressure.

The advantages of the present invention with respect to the prior art are many. They include the following:

1. Heavy lifting of the supply solution to a high level is no longer required.

2. The heat bag can be filled more quickly since the pressure during this process can be higher.

3. The discharge bag can be emptied into a waste located at a higher position.

4. The discharge bag comprises slag product which make the fluid more viscous, such as fibrin precipitates, etc., but by using a higher pump pressure the extraction can occur more quickly.

5. Both the supply and extraction pressure to the patient can be adjusted according to that which the patient feels is comfortable.

6. The dialysis solution is always located inside bags and tubes which can be manufacture from cheap plastic material according to known techniques. The pump arrangement according to the invention only acts upon the outside of these bags. The PD-solution is located in a closed system for the whole time.

7. The apparatus according to the present invention is simple and can be manufactured compactly and lightly, which means that it can easily be transported.

8. The apparatus is very flexible and can use combinations of forced supply and supply by means of gravity.

9. The apparatus according to the present invention can work without appreciable energy consumption. The energy consumption can additionally be reduced so that the apparatus, for instance, during a power outage, can operate for a longer time using reserve power, such as batteries.

10. Additional energy saving can be made via heat exchanging of the warm dialysis solution in the discharge bag with colder fresh PD-solution in the heat bag.

BRIEF DESCRIPTION OF THE DRAWINGS

Further objects, advantages and features of the invention will appear from the following detailed description of the invention with reference to certain preferred embodiments of the invention shown in the accompanying drawings, in which FIG. 1 is a front, perspective view of a PD-cycler according to the applicant's earlier known GAMBRO PD 100 system.

FIG. 2 is a side elevational view of a tube-set for use in the GAMBRO PD 100 system.

FIG. 3 is a front, perspective view of an apparatus according to the present invention.

FIG. 4 is a front, perspective view similar to that in FIG. 3 of an alternative apparatus according to the present invention.

FIG. 5 is a side elevational view of a tube-set for use with the apparatus according to the present invention.

FIG. 6 is a side elevational view of an alternative tube set for use with the apparatus according to the present invention.

FIG. 7 is a side elevational view of a simplified tube-set for use with the apparatus according to the present invention.

FIG. 8 is a schematic view of a preferred pump arrangement for the apparatus according to the present invention, and FIG. 9 is a schematic view of a second pump arrangement for the apparatus according to the present invention.

DETAILED DESCRIPTION

Referring to the figures, in which like reference numerals refer to like elements thereof, FIG. 1 shows an apparatus according to GAMBRO PD 100 system. The apparatus comprises a stand 1 supported at the base by five wheel arrangements 2. The stand comprises a vertical column 3 which is about 2 meters high. AT the upper end there are several hook arrangements 4 for hanging up supply bags 5 containing dialysis solution. On an intermediate level of the stand there is a holder (not shown) for a regulating unit 6. AT the bottom of the stand there is an additional holder 18 for a valve device 14.

The regulating unit 6 comprises scales 7, on which a heat bag 8 is positioned. The scales 7 are coupled to a load cell which measures the weight of the contents in the heat bag 8. On the regulating unit's 6 front side there are push buttons and displays which are used in order to control and reset the operating condition of the apparatus. The regulating unit 6 further comprises a valve arrangement 9 intended to operate on the tubes which connect the supply bags 5 with the heat bag 8.

The regulating unit 6 is further provided with a hook device 10 which is connected with the aforementioned load cell. A carrier device 11 is hung on the hook arrangement 10, said carrier arrangement supporting a discharge bag 12 at its lower end.

The supply bags 5, the heat bag 8, a catheter 13 entered into the abdominal cavity of the patient, the discharge bag 12 and a collection bag 16 are connected by means of a tube-set 20 which is shown in more detail in FIG. 2, and described below.

The holder 18 at the bottom end of the stand further comprises a valve arrangement 14 which is controlled by the regulating unit via a cable 15.

The valve arrangements 9 and 14 are double valve devices which clamp around the tubes which pass through the valve arrangements and thereby perform valve functions. The function of the valve arrangements 9 and 14 is such that when the one valve of each valve arrangement, 9 and 14, is opened, the corresponding other valve is closed.

As is clear from FIG. 1 the supply bags 5 are connected to heat bag 8 by a first tube 21 which passes through the valve arrangement 9. The heat bag 8 is connected with the patient's catheter 13 via a second tube 22 which also passes through the valve arrangement 9. The patient's catheter 13 is connected with the discharge bag 12 by means of a third tube 23 and the discharge bag 12 is connected with the collection bag 16 through a fourth tube 24, whereby the third and the fourth tube pass through the second valve arrangement 14.

The tube-set 20 is shown in more detail in FIG. 2. In this figure five connectors 25 are shown for five supply bags. The connectors 25 are connected with the first tube 21 by several tubes and a branch of manifold coupling 29. The outlet from each supply bag is regulated by a tube clamp 26. The first tube 21 and the second tube 22 are connected with each other by a Y-coupling which then leads further to the heat bag 8. The first tube 21 has a clamp arrangement 9a and the second tube 22 has a clamp arrangement 9b, which are included in the first valve arrangement 9. The second tube 22 and the third tube 23 are connected to each other with a T-coupling which leads to a connector 27 to the patient's catheter. The tube between the connector 27 and the T-coupling can be of the double-type with separate inlet and outlet, or a so-called double-lumen tube. The third tube 23 and the fourth tube 24 are connected with each other by a Y-coupling which is further connected with the discharge bag 16. The third tube 23 has a clamp arrangement 14a and the fourth tube 24 has a clamp arrangement 14b which constitutes the second valve arrangement 14.

The fourth tube 24 ends with a connector 28 to a collection bag. A plurality of clamp arrangements similar to the clamp 26 are found at different locations on the tubes in order to allow manual maneuvering and throttling of corresponding tubes.

The function of the PD 100 system as described above is as follows.

Filling of the heat bag (HF, Heater Fill)

When the valve arrangement 9 is in its first open position, the tube 21 is open. The dialysis solution is thereby fed from the supply bags 5 to the heat bag 8 by means of gravity. When the heat bag 8 is filled by the required amount, the valve arrangement 9 is closed and a measured amount of dialysis solution is stored in a memory of the regulating unit 6. The heat bag 8 is continually heated by a heat element 17 positioned in the scales 7 until the desired temperature has been reached.

Extraction of dialysis solution (PD, Patient Drain)

When the second valve arrangement 14 is in its first open position, the tube 23 is opened and connects the catheter 13 with the discharge bag 12. In this way, used dialysis solution is drained by means of gravity from the catheter 13 to the discharge bag 12. After a predetermined time the valve arrangement 14 is closed and collected dialysis solution in the discharge bag 12 is weighed with the help of the load cell in the regulating unit 6 and is stored in the regulating unit's memory.

Supply of dialysis solution (PF, Patient Fill)

When the first valve arrangement 9 is in its second open position the tube 22 is open and connects the heat bag 8 with the catheter 13. The warm contents in the heat bag is supplied to the patient by means of gravity. Any remaining dialysis solution in the heat bag is registered with the help of the weighing device.

Draining of the discharge bag (SD, System Drain)

When the second valve arrangement 14 is in its second opened position, the tube 24 is open and connects the discharge bag 12 with the collection bag 16 and the contents in the discharge bag 12 is drained to the collection bag 16. The tube 24 can similarly be connected to a drain or waste. The collection bag 16 can consist of used supply bags 5 or a larger collection vessel, in accordance with requirements.

FIG. 3 shows an apparatus according to the present invention. The apparatus can be used with the tube-set which is shown in FIG. 2 and the supply bags and fluid containers which can be seen in FIG. 1. The components of the apparatus according to FIG. 3, which are identical or which correspond to components which are shown in the apparatus according to FIG. 1, have been given the same reference numerals as in FIG. 1 but increased by 30, i.e., the heat bag 8 according to FIG. 1 has now been given the reference numeral 38 in FIG. 3.

The difference between the apparatus according to FIG. 3 and the apparatus according to FIG. 1 is that the discharge bag 42 has been placed on top o the heat bag 38 and the second valve arrangement 44 has been attached to the regulating unit 36. Furthermore, the scales 37 have been provided with a cover so that the scales and the cover together form a case which surrounds the heat bag and the discharge bag.

The apparatus according to FIG. 3 thus comprises a regulating unit 36 with a first valve arrangement 39 and a second valve arrangement 44. The first tube 21 passes through the valve arrangement 39 to a heat bag 38 positioned on the scales 37. The second tube 22 leads from the heat bag 38 through the valve arrangement 39 to a patient. The third tube 23 leads from the patient through the second valve arrangement 44 to a discharge bag 42 positioned on the scales 37. The fourth tube 24 leads from the discharge bag 42 via the second valve arrangement 44 to a waste or collection bags.

The regulating unit 36 further comprises, in accordance with the invention, a case 50 positioned above the scales 37. The case 50 tightly conforms to the appearance and form of the scales 37 such that a sealed space is formed between the case 50 and the scales 37. The case 50 is provided with locking means 51 for secure attachment of the case 50 to the scales 37. The case can be completely removable or can be foldable by means of hinges in a convenient manner. Additionally, there are seals 52 between the case and the scales.

The tube from the heat bag 38 and from the discharge bag 42 passes through the wall of the case by means of sealed holes 53 and 54. The case 50 is further provided with a connection 55 for a tube 56, which leads to a pump 57 arranged on the regulating unit 36. The pump can be positioned inside the regulating unit 36.

The function of the apparatus according to FIG. 3 is in principle the same as that described above for the GAMBRO PD 100 system. However, transport of the dialysis solution occurs by means of positive and negative pressure inside the case 50.

An example of a treatment starts with filling of the heat bag (HF) by bringing a negative pressure into the case 50 by means of the pump 57 via conduit 56 and the connection 55. At the same time, the tube 21 is opened by means of the valve arrangement 39 and fresh dialysis fluid flows from the supply container to the heat bag 38. When the heat bag 38 is filled by a desired amount, which is determined by weighing of the heat bag 38, the valve 39 is closed. The contents of the heat bag is heated, by means of an in-built heat element in the scales 37 (not shown in FIG. 3), to the desired temperature.

Then, the catheter in a connected patient is joined with the discharge bag 42 by placing the second valve arrangement 44 in its first open position and used dialysis fluid is extracted from the patient (PD, Patient Drain) by the application of a negative pressure in the case. The amount of extracted solution is then weighed.

The catheter in the patient is then joined with the heat bag 38 by placing the first valve arrangement 39 in its second open position for supplying fresh dialysis solution (PF), by means of an overpressure in the case. When a suitable volume has been supplied to the patient, the first valve arrangement 39 is closed.

The discharge bag is finally connected with a drain or a collection bag by placing the second valve arrangement 44 in its second open position and an overpressure is applied in the case for releasing the used dialysis solution (SD).

The above described cycle can be modified in different ways according to which manner is applicable in a particular case. It is thus normally suitable if a supply to the patient (PF) follows immediately after extraction from the patient (PD) so that the patient receives fresh dialysis solution as quickly as possible. It is also preferable if the heat bag is filled (HF) before draining of the discharge bag (SD) since the heat bag is given a sufficiently long heating time thereby. In this way the heat contents in the discharge bag can be used to heat the contents in the heat bag, which reduces energy consumption.

According to a preferred embodiment of the present invention it can, however, be advantageous to reverse HF and SD so that drawing of the discharge bag (SD) occurs before filling of the heat bag (HF), as first described. The reason for this is that the pressure in the case then only has to be changed once during each cycle from negative pressure during filling of the heat bag and thereafter immediately following extraction of the used dialysis solution from the patient to a positive pressure for supplying fresh dialysis solution to the patient (PF), upon which the contents in the discharge bag is drained (SD). In this way a smaller amount of pressure medium is consumed which leads to lower energy consumption. Additionally, pumps with lower capacity can be used which have a lower noise level.

It is also possible to use the apparatus according to the present invention in such a way that extraction of the dialysis solution from the patient (PD) occurs with the help of gravity, as in the earlier known GAMBRO PD 100 system. For this, one uses a discharge bag 12 hung on a hook by means of a carrier arrangement, as in the earlier known GAMBRO PD 100 system. Supply of fresh dialysis solution (PF) occurs, however, with the help of an overpressure on the heat bag. In this embodiment only an overpressure on the heat bag is required, whereby the case can then be flexible and consist of a bellows arrangement. The pressure can also be exerted by some type of mechanical arrangement, such as springs or weights, etc.

In an alternative embodiment of the present invention as shown in FIG. 4, the heat bag 38 and the discharge bag 42 are replaced by a ready-prepared double supply bag which is placed inside the case 50. After heating, the contents in the supply bag 5 are emptied directly to the patient by exerting an overpressure in the case 50. In this embodiment neither the first tube 21 nor the fourth tube 24 are required. The supply bag does not need to be emptied completely with each cycle, but smaller amounts can be taken out during each cycle (tidal). Neither does the drain part of the bag need to be filled during each cycle, but can accumulate increasing amounts for each cycle until it is full. For example, the bag can contain 4.5 liters of fresh dialysis solution from the start and no used dialysis solution and then can be emptied in small amounts during each cycle, whereby the used dialysis solution goes into the thus successively increasing discharge portion of the bag. When all of the fresh dialysis solution has been used, the case 50 is opened, whereupon the old supply bag is discarded and a new supply bag is applied to the apparatus in accordance with the invention.

FIG. 5 shows a tube-set intended for use together with the apparatus according to FIG. 3. The components of the tube-set according to FIG. 5, which are identical with, or correspond to, the components which are shown in FIG. 2, have been given the same reference numerals but with the addition of "a". Thus the tube-set 20a according to FIG. 5 comprises connectors 25a to supply bags as well as tube clamps 26a. Tubes from the connectors 25a are coupled together with a branch coupling 29a, which leads to the first tube 21a. The first tube 21a and the second tube 22a are joined to each other by an F-coupling 30. The F-coupling is connected with the heat bag 38a via a tube 31 provided with a tube clamp. The tube 31 passes into a bushing 53a corresponding to the hole 53 of FIG. 3. The second tube 22a and the third tube 23a are connected to each other by a Y-coupling 32 which is connected through tube 33 to a connector 27a to a catheter. The tube 33 is provided with an optional inlet 34 for an infusion fluid. The third tube 23a is connected with a fourth tube 24a leading to the waste by an F-coupling 35, which furthermore is connected with the discharge bag 42a by a tube 40 provided with a bushing 54a corresponding to the hole 54 of FIG. 3. The tube-set 20a is provided with a plurality of color codings in order to simplify the connection, as is known.

FIG. 6 shows a tube-set 20b similar to the tube-set 20a according to FIG. 5 whereby the same components have been given the suffix "b". The difference with respect to FIG. 5 is that the heat bag and the discharge bag have been combined as a single double bag 70. The double bag 70 has a first conduit 71 connected with a first chamber of the double bag 70 and a second connection 72 connected with a second chamber of the double bag 70. Additionally, connectors 25b are provided for ten supply bags. The function is clear from the above description of FIG. 3 and 5.

FIG. 7 shows a third tube-set 20c, particularly adapted for use together with the alternative embodiment of the apparatus according to FIG. 4, whereby the same components as in FIGS. 5 and 6 have been given the suffix "c". A double bag 70c corresponding to the double bag 70 according to FIG. 6 and provided with two connections 71c and 72c is used. The connections are joined with the second tube 22c and the third tube 23c respectively which, via a Y-coupling, lead to a connector 27c to the patient's catheter. The tube-set according to FIG. 7 is very simple and cheap to manufacture.

If the connection 71c and the connection 72c are on the same side of the bag, the bushings 53c and 54c can be combined into a common bushing which reduces the risk of leakage during operation of the apparatus. Additionally, double-lumen tubes can be used as described in European Patent No. 499,718. In this way the tube-set can be additionally simplified.

FIG. 3 shows a pump 57 for supplying air to the inside of the case 50. The pump 57 is arranged to provide a positive or negative pressure within the range of from about −0.3 bar to +0.3 bar. The pressure which the pump is able to achieve is defined by the construction of the pump and the rotational speed. Suitable values of the rotational speed can be stored in the memory of the regulating unit 36.

It is clear that different pressures can be used for the four different cycles. During filling of the heat bag from the supply bags, it is desirable that filling occurs quickly, for which reason an underpressure of e.g. −0.3 bar can be used. The filling is continually monitored by the weighing device. When a predetermined amount has entered the heat bag, the filling is stopped.

Supply of fresh dialysis solution to the patient (PF) should occur as quickly as possible, without however, subjecting the patient to discomfort. A suitable overpressure in the case can be about 0.1 bar. The supply pressure can be greater at the start of supplying and then reduced towards the end of supplying. The supply flow is continually monitored by means of the weight reduction of the heat bag. If the abnormal conditions occur, the apparatus can stop the supply. For example, pressure during supply can be high, without any supply occurring, which indicates that the catheter is blocked. Suitable relationships between the supply pressure and the flow can be programmed into the memory of the apparatus.

Extraction of used dialysis fluid from the patient (PD) occurs with a moderate underpressure of somewhere around −0.05 bar. The extraction of the dialysis solution from the patient is also monitored continually with the weighing device for checking a suitable relationship between the extraction pressure and flow. If abnormal conditions are present, the extraction is stopped. The relationship between the extraction pressure and flow can be programmed into the memory of the apparatus.

Draining of used dialysis solution from extraction bag (SD) occurs at a relatively high pressure of e.g. 0.3 bar so that extraction occurs as quickly as possible.

Preferred supply pressure and extraction pressure as well as flow speeds can be pre-programmed into a separate memory positioned on a so-called smart card which is specifically for the patient. This smart card additionally comprises other parameters in order to operate the apparatus according to the invention depending on the specific requirements of the patient. The card is programmed by the patient's doctor or dialysis nurse in accordance with his prescription and is entered into the apparatus for use. The programming can occur in connection with some type of evaluation system for PD-dialysis, such as GAMBRO evaluation computer programs, Patient Dialysis Capacity, (PDC).

The pump 57 is suitably a centrifugal pump which achieves a suitable output pressure of e.g. maximum 0.3 bar. By regulating the cyclic speed and the rotational direction of the pump, the pressure which is supplied to the case can be varied between −0.3 bar and +0.3 bar relative to the surrounding atmosphere. By reversing the rotational direction a negative pressure is obtained.

Alternatively, the change of the direction of pressure (positive or negative pressure relative to the surrounding atmosphere) can occur by means of a valve arrangement, as shown in FIG. 8.

In the first and preferred embodiment of the pump arrangement, the case 50 is provided with a second opening 70, in addition to holes 53 and 54. Opening 70 is connected to a damping volume 71 having a sufficient volume for damping any pressure surges occurring during valve or pump operation. Damping chamber 71 is connected to two valves, 72 and 73, and further to a muffler 74 being connected to the atmosphere by a tube 75.

Interposed between valves 72 and 73 is a pump 76, preferably a membrane pump, although any suitable pump which achieves a sufficient output pressure can be used, provided it is sufficiently silent. The pump 76 is connected to the chassis of the apparatus by means of dampening springs 77 and 78 shown as rubber spring elements of an omega shape. The spring members dampen any transmission of structural vibrations from the pump to the apparatus. Any sound passing from the pump to the surroundings via the tubes must pass the muffler 74, which dampens such sound or vibrations.

Particle filters 79 and 80 are inserted in the tubes in a suitable position for preventing particles from entering pump 76. A suitable filter size is about 40 microns.

Valves 72 and 73 are operated for connecting pump 76 for positive or negative pressure in the case. In FIG. 8 are shown the positions for negative pressure for filling the heater bag 38 with fresh solution. By reversing the direction of valves 72 and 73, the opposite operation takes place.

The correct operation of the pump system is monitored by a pressure sensor 81. Sensor 81 is connected to a microcomputer controlling the overall apparatus, specifically valves 72 and 73 and pump 76. The rotational speed of pump 76 is controlled in order to obtain a desired positive or negative pressure, which is monitored by pressure sensor 81. A bleeding valve 82 is connected in a shunt line, connecting the case 50 with the atmosphere via tube 75 in certain occasions. Bleed valve 82 is normally open if not activated by an electric current.

The pump arrangement is also provided with a protective system shown as a pressure sensor 83 and a bleed valve 84 connecting damping chamber 71 with the atmosphere at fault conditions. The protective system can, if desired, be connected directly to case 50 via a tube 85 (shown by dashed lines in FIG. 8).

Muffler 74 is shown as a cylindric vessel provided with an inlet tube 75 and an outlet tube 86. Muffler 74 has thick walls and is made of a plastic material. Since the air must pass a long distance inside muffler 74, sound is damped and absorbed. Any type of muffler or silencer can be used.

Case 50 is supported by a single shaft 87 guided by bearings 88 and moveable in the vertical direction. The lower end of the shaft 87 is supported by a load cell 89, emitting an electric signal, the size of which is dependent of the pressure exerted by shaft 87 on the upper side of load cell 89. This technique is well known.

In a second embodiment of the pump arrangement as shown in FIG. 9, another arrangement is used to achieve positive and negative pressure in the case. The pump arrangement comprises two pressure chambers 60 and 61, in which overpressure and underpressure respectively prevail. The pressure chambers are connected selectively with the case according to the desired functional scheme by means of a three-way valve 62. The volume and the pressure in the pressure chambers are dimensioned so that a complete cycle can be performed. For example the overpressure can be about 2 bar and the underpressure about −0.9 bar relative to atmosphere. In this way the pressure chambers have a combined volume which is about 5 liters, but still at least a complete cycle can be carried out with the contents in these pressure chambers without the help of a pump. In this way it can be ensured that the apparatus can operate during a longer period in the event of a power break and can be operated with only in-built batteries and a minimum of power consumption, i.e. the pump does not need to be operated.

A pump 63 is arranged between the pressure chambers 60 and 61 in order to form and maintain the pressure in these chambers. The pump can be dimensioned for continual operation and has a large amount of time in order to build up the necessary pressure between the cycles for PD-treatment. Thus, a pump can be used which is practically silent. The pump can be started a suitable time before an exchange is to take place, for example 20 minutes before. During 20 minutes, the pump builds up the necessary pressures inside chambers 60 and 61. The volumes and pressures of chambers 60 and 61 are sufficient for performing the operation without any net flow from the pump. However, the pump is still operated for increasing the available amount of air and pressure. In this way, a very small and silent pump can be used.

The pressure regulation valves 64 and 65 connect the input side and the output side respectively of the pump to atmosphere. The pressure regulation valves are adjusted to the aforementioned exemplifying values of −0.9 bar and 2 bar so that these pressures are obtained as the pump works.

For reasons of safety the case is provided with pressure relief valves 67 and 68, which ensure that the case cannot be pressurized with too large a pressure.

A pressure sensor 66 is positioned in the conduit to the case and gives a pressure signal to the microcomputer which regulates the function of the apparatus and particularly the valve 62 which comprises pressure reduction arrangements to regulate the pressure which is supplied from the pressure chambers to the case.

Even if a gas, particularly air, is preferred as the pressure medium it is also possible to use fluids such as water. It is then important that the case 50 is completely airtight, since suction of air during underpressure in the case would disturb the operation.

The upper part of the case can be transparent so that the function of the apparatus can be observed from the outside. In this way it can be determined whether the bags have become blocked in some way or whether other types of risk for incorrect operation are present, which increases the safety of the apparatus.

It is also possible to exert pressure on the bags 38 and 42 by means of some mechanical arrangement such as lever arms, springs and/or weights.

Since the heat bag 38 as well as the collection bag 42 are positioned on the same scales, the advantage is obtained that the same measurement cell measures the contents of both bags which reduces possible measurement errors.

Additional safety devices can be used on the tube-set in order to ensure that the patient is not subjected to too high a pressure, such as hydrophobic filter arrangements, pressure boxes with micro-switches etc. Such devices are already known in the art and can be used by a skilled man.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:
1. An apparatus for conducting peritoneal dialysis comprising at least one flexible container for handling a fluid useful in said peritoneal dialysis, supply means for supplying said fluid to said at least one flexible container, weighing means for weighing the contents of said at least one flexible container, a conduit connected to said at least one flexible container for conducting a flow of said fluid, enclosure means surrounding said at least one flexible container thereby forming a space between said at least one flexible container and said enclosure means, and pressure control means for altering the pressure within said space for transferring said fluid from said at least one flexible container through said conduit.

2. The apparatus of claim 1, wherein said enclosure means includes an entry port for permitting said conduit to pass through said enclosure means.

3. The apparatus of claim 2, wherein said entry port includes entry port sealing means for sealing said entry port with respect to said conduit.

4. The apparatus of claim 1, wherein said pressure control means comprises pressure increasing means for creating a pressure greater than atmospheric pressure within said space for emptying said fluid from said at least one flexible container through said conduit.

5. The apparatus of claim 1, wherein said enclosure means is rigid, and wherein said pressure control means comprises pressure decreasing means for creating a pressure less than atmospheric pressure within said space for driving said fluid into said at least one flexible container through said conduit.

6. The apparatus of claim 4 or 5 wherein said space includes a pressure medium comprising a gas.

7. The apparatus of claim 6, wherein said gas comprises air.

8. The apparatus of claim 4 or 5, wherein said space includes a pressure medium comprising a liquid.

9. The apparatus of claim 8, wherein said liquid comprises water.

10. The apparatus of claim 1, wherein said enclosure means comprises a cover movable between an open and a closed position, and including sealing means for sealing said cover when in said closed position.

11. The apparatus of claim 1, wherein said at least one flexible container comprises first and second flexible containers, wherein said conduit comprises a first conduit for connection to said first flexible container, and including a second conduit connected to said second flexible container for conducting a flow of fluid.

12. The apparatus of claim 11, wherein said first flexible container is adapted for handling a fresh fluid, and said second flexible container is adapted for handling a used fluid.

13. The apparatus of claim 1, including valve means associated with said conduit for controlling the flow of said fluid in said conduit.

14. The apparatus of claim 1, wherein said at least one flexible container comprises a plastic bag.

15. The apparatus of claim 1, wherein said space includes a pressure medium, and wherein said pressure control means includes a pump for controlling the flow of said pressure medium into and out of said space.

16. The apparatus of claim 15, including damping means for damping vibrational movements created by said pump.

17. The apparatus of claim 16, including muffler means for reducing the sound level of said pump.

18. The apparatus of claim 15, wherein said pump has an output pressure which is dependent upon the cycle speed thereof.

19. The apparatus of claim 18, wherein said pump comprises a centrifugal pump.

20. The apparatus of claim 1, wherein said pressure control means comprises a first pressure chamber including a gas maintained at a pressure greater than atmospheric pressure and a second pressure chamber including a gas maintained at a pressure less than atmospheric pressure, and valve means for selectively connecting said first and second pressure chambers with said enclosure means.

21. The apparatus of claim 20, wherein said pressure control means includes a pressure sensor for controlling said valve means.

22. The apparatus of claim 20, wherein said pressure control means includes a pump in communication with said first and second pressure chambers for increasing the pressure in said first pressure chamber and decreasing the pressure in said second pressure chamber, first pressure chamber valve means for regulating the pressure in said first pressure chamber and second pressure chamber valve means for regulating the pressure in said second pressure chamber.

23. The apparatus of claim 22, wherein said pump operates substantially continuously.

24. The apparatus of claim 20, including pressure relief means for maintaining the pressure within said enclosure means between predetermined limits.

25. The apparatus of claim 24, wherein said predetermined limits are between about 0.3 bar and −0.3 bar.

* * * * *

UNITED STATES PATENT AND TRADEMARK OFFICE
Certificate

Patent No. 5,722,947                                                                                      Patented: March 3, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jan-Bertil Jeppsson, Lomma, Sweden; Tor Nordlie, Eslov, Sweden; and Joakim Oscarson, Kristianstad, Sweden.

Signed and Sealed this First Day of June 2004.

BRIAN L. CASLER
*Supervisory Patent Examiner*
Art Unit 3763